(12) United States Patent
Roy et al.

(10) Patent No.: US 9,089,292 B2
(45) Date of Patent: Jul. 28, 2015

(54) CALIBRATION OF GLUCOSE MONITORING SENSOR AND/OR INSULIN DELIVERY SYSTEM

(75) Inventors: Anirban Roy, Encino, CA (US); Barry Keenan, Hollywood, CA (US); Michael Kremliovsky, Poway, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 933 days.

(21) Appl. No.: 12/748,341

(22) Filed: Mar. 26, 2010

(65) Prior Publication Data

US 2011/0237917 A1  Sep. 29, 2011

(51) Int. Cl.
| | |
|---|---|
| *A61B 5/00* | (2006.01) |
| *A61B 5/145* | (2006.01) |
| *A61B 5/1486* | (2006.01) |
| *A61B 5/1495* | (2006.01) |

(52) U.S. Cl.
CPC .......... *A61B 5/14532* (2013.01); *A61B 5/1495* (2013.01); *A61B 5/14865* (2013.01); *A61B 5/4839* (2013.01); *A61B 5/6849* (2013.01); *A61B 5/1451* (2013.01); *A61B 2560/0223* (2013.01)

(58) Field of Classification Search
CPC ................... A61B 5/14532; A61B 5/14865
USPC .......................................................... 600/365
See application file for complete search history.

(56) References Cited

U.S. PATENT DOCUMENTS

| | | | |
|---|---|---|---|
| 5,391,250 A | 2/1995 | Cheney, II et al. | |
| 6,254,586 B1 | 7/2001 | Mann et al. | |
| 6,360,888 B1 | 3/2002 | McIvor et al. | |
| 6,424,847 B1 | 7/2002 | Mastrototaro et al. | |
| 6,641,533 B2 | 11/2003 | Causey, III et al. | |
| 6,895,263 B2 | 5/2005 | Shin et al. | |
| 7,394,046 B2 * | 7/2008 | Olsson et al. ................. 244/3.1 |
| 7,833,157 B2 | 11/2010 | Gottlieb | |
| 2002/0111547 A1 | 8/2002 | Knobbe et al. | |
| 2002/0161288 A1* | 10/2002 | Shin et al. ..................... 600/316 |
| 2003/0018457 A1* | 1/2003 | Lett et al. ........................ 703/11 |
| 2004/0153430 A1* | 8/2004 | Sayad ............................. 706/61 |

(Continued)

FOREIGN PATENT DOCUMENTS

| | | |
|---|---|---|
| WO | WO/2005/057175 | 6/2005 |
| WO | WO/2006/099151 | 9/2006 |

(Continued)

OTHER PUBLICATIONS

Van Den Berghe, Greet, et al., "Intensive Insulin Therapy in Critically Ill Patients" The New England Journal of Medicine, vol. 345, No. 19, Nov. 8, 2001, pp. 1359-1367.

(Continued)

*Primary Examiner* — Etsub Berhanu
(74) *Attorney, Agent, or Firm* — Berkeley Law & Technology Group, LLP

(57) ABSTRACT

Disclosed are methods, apparatuses, etc. for calibrating glucose monitoring sensors and/or insulin delivery systems. In certain example embodiments, blood glucose reference samples may be correlated with sensor measurements with regard to a delay associated with the sensor measurements. In certain other example embodiments, one or more parameters of a probability model may be estimated based on blood glucose reference sample-sensor measurement pairs. Based on such information, function(s) for estimating a blood-glucose concentration in a patient may be determined.

27 Claims, 20 Drawing Sheets

(56) References Cited

U.S. PATENT DOCUMENTS

| | | |
|---|---|---|
| 2005/0027180 A1 | 2/2005 | Goode |
| 2008/0221509 A1 | 9/2008 | Gottlieb et al. |
| 2009/0105573 A1* | 4/2009 | Malecha ............ 600/365 |
| 2009/0112478 A1 | 4/2009 | Mueller, Jr. |
| 2009/0192366 A1 | 7/2009 | Mensinger |
| 2009/0198118 A1 | 8/2009 | Hayter et al. |

FOREIGN PATENT DOCUMENTS

| | | |
|---|---|---|
| WO | WO 2009047569 A2 * | 4/2009 |
| WO | WO/2011/119201 | 9/2011 |

OTHER PUBLICATIONS

PCT/US2011/000477 PCT application as filed on Mar. 15, 2011, 80 pages.
PCT/US2011/000477 Initial Publication without International Search Report on Sep. 29, 2011, 80 pages.
PCT/US2011/000477 International Search Report mailed Nov. 22, 2011, 7 pages.
EP/11713100/115.P008PCTEP, Communication under Rule 71#) EPC re intention to grant European patent dated Mar. 13, 2015, 154 pages.

* cited by examiner

CALIBRATION OF GLUCOSE MONITORING SENSOR AND/OR INSULIN DELIVERY SYSTEM

BACKGROUND

1. Field

Subject matter disclosed herein relates to calibrating a glucose monitoring sensor and/or an insulin delivery system including, by way of example but not limitation, calibration that is at least partially automatic and/or a calibration of sensor current measurements during operation.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type I diabetes mellitus (or in some cases, if β-cells produce insufficient quantities of insulin, a condition known as Type II diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetics. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type I diabetics in the United States were using infusion pump therapy. Presently, over 7% of the more than 900,000 Type I diabetics in the U.S. are using infusion pump therapy. The percentage of Type I diabetics that use an infusion pump is growing at a rate of over 2% each year. Moreover, the number of Type II diabetics is growing at 3% or more per year, and growing numbers of insulin-using Type II diabetics are also adopting infusion pumps. Additionally, physicians have recognized that continuous infusion can provide greater control of a diabetic's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, upon blood glucose measurements obtained from an embedded blood-glucose sensor in, e.g., real-time. Closed-loop infusion pump systems may also employ the delivery of glucagon, in addition to the delivery of insulin, for controlling blood-glucose and/or insulin levels of a patient (e.g., in a hypoglycemic context).

SUMMARY

Briefly, example embodiments may relate to methods, systems, apparatuses, and/or articles, etc. for calibrating glucose monitoring sensors and/or insulin delivery systems. Glucose monitoring sensors and/or insulin delivery systems, including those that are designed to operate continually (e.g., repeatedly, at regular intervals, at least substantially continuously, etc.), may be calibrated. More specifically, but by way of example only, such calibration may be at least automatic or semi-automatic and/or calibration of sensor current measurements may be performed online (e.g., during operation of an associated system).

In one or more example embodiments, a method may include: correlating blood glucose reference samples with sensor measurements to provide at least one output signal responsive to a delay associated with the sensor measurements; and determining a function for estimating a blood-glucose concentration in a patient from sensor measurements based, at least in part, on the at least one output signal.

In at least one example implementation, the correlating may further include: applying the blood glucose reference samples and the sensor measurements to a matched filter at multiple time shift delays to ascertain the delay. In at least one other example implementation, the correlating may further include: correlating the sensor measurements with the blood glucose reference samples at multiple different time delays to ascertain the delay. In at least one other example implementation, the determining may further include: applying the blood glucose reference samples and the sensor measurements to a Wiener filter in conjunction with the delay to determine multiple filter coefficients.

In at least one other example implementation, the determining may further include: determining a function for estimating a blood-glucose concentration in the patient from sensor measurements based, at least in part, on a noise signal that is associated with the sensor measurements. In at least one other example implementation, the sensor measurements may comprise current sensor measurements taken from interstitial fluid of the patient. In at least one other example implementation, the determining may further include: determining a function for estimating a blood-glucose concentration in the patient, the function to account for the delay; the delay representing, at least partially, an approximated delay associated with blood glucose diffusion between one or more blood vessels and interstitial fluid of the patient.

In at least one other example implementation, the determining may further include: determining a slope and an offset for the function for estimating a blood-glucose concentration in a patient. In yet at least one other example implementation, the determining may further include: determining the slope and the offset for the function using a Bayesian technique in which a parameter vector includes a calfactor variable and an offset variable and in which an independent variable includes a current signal corresponding to the sensor measurements. In yet at least one other example implementation, the determining may further include: determining the slope and the offset for the function using a linear Kalman filter technique in which a parameter vector includes a calfactor variable and an offset variable.

In at least one other example implementation, the method may further include: taking the sensor measurements that are to be correlated using one or more subcutaneous current sensors; and infusing insulin into the patient based on the function for estimating a blood-glucose concentration in the patient.

In one or more example embodiments, an apparatus may include a filter unit to receive one or more signals based on blood-glucose sensor measurements, the filter unit may include one or more processors to: correlate blood glucose reference samples with sensor measurements to provide at least one output signal responsive to a delay associated with the sensor measurements; and determine a function for estimating a blood-glucose concentration in a patient from sensor measurements based, at least in part, on the at least one output signal.

In at least one example implementation, the filter unit may be capable of correlating the blood glucose reference samples with the sensor measurements by: applying the blood glucose reference samples and the sensor measurements to a matched filter at multiple time shift delays to ascertain the delay. In at least one other example implementation, the filter unit may be capable of correlating the blood glucose reference samples with the sensor measurements by: correlating the sensor measurements with the blood glucose reference samples at multiple different time delays to ascertain the delay. In at least one other example implementation, the filter unit may be capable of determining the function for estimating the blood-glucose concentration in the patient by: applying the blood glucose reference samples and the sensor measurements to a Wiener filter in conjunction with the delay to determine multiple filter coefficients.

In at least one other example implementation, the filter unit may be capable of determining the function for estimating the blood-glucose concentration in the patient by: determining a function for estimating a blood-glucose concentration in the patient from sensor measurements based, at least in part, on a noise signal that is associated with the sensor measurements. In at least one other example implementation, the sensor measurements may comprise current sensor measurements taken from interstitial fluid of the patient. In at least one other example implementation, the filter unit may be capable of determining the function for estimating the blood-glucose concentration in the patient by: determining a function for estimating a blood-glucose concentration in the patient, the function to account for the delay; the delay representing, at least partially, an approximated delay associated with blood glucose diffusion between blood vessels and interstitial fluid of the patient.

In at least one other example implementation, the filter unit may be capable of determining the function for estimating the blood-glucose concentration in the patient by: determining a slope and an offset for the function for estimating a blood-glucose concentration in a patient. In yet at least one other example implementation, the filter unit may be capable of determining the function for estimating the blood-glucose concentration in the patient by: determining the slope and the offset for the function using a Bayesian technique in which a parameter vector includes a calfactor variable and an offset variable and in which an independent variable includes current signal corresponding to the sensor measurements. In yet at least one other example implementation, the filter unit may be capable of determining the function for estimating the blood-glucose concentration in the patient by: determining the slope and the offset for the function using a linear Kalman filter technique in which a parameter vector includes a calfactor variable and an offset variable.

In at least one other example implementation, the apparatus may further include: one or more blood-glucose subcutaneous current sensors adapted to be coupled to the patient to obtain blood-glucose sensor measurements and adapted to provide the one or more signals based on the blood-glucose sensor measurements; with the filter unit being capable of obtaining the blood-glucose sensor measurements via the one or more blood-glucose subcutaneous current sensors using the one or more signals; and at least one insulin delivery system adapted to infuse insulin into the patient based on the function for estimating a blood-glucose concentration in the patient.

In one or more example embodiments, a system may include: means for correlating blood glucose reference samples with sensor measurements to provide at least one output signal responsive to a delay associated with the sensor measurements; and means for determining a function for estimating a blood-glucose concentration in a patient from sensor measurements based, at least in part, on the at least one output signal.

In one or more example embodiments, an article may include at least one storage medium having stored thereon instructions executable by one or more processors to: correlate blood glucose reference samples with sensor measurements to provide at least one output signal responsive to a delay associated with the sensor measurements; and determine a function for estimating a blood-glucose concentration in a patient from sensor measurements based, at least in part, on the at least one output signal.

In one or more example embodiments, a method may include: obtaining multiple blood glucose reference sample-sensor measurement pairs; estimating one or more parameters of a probability model based, at least in part, on the blood glucose reference sample-sensor measurement pairs; and determining a function for estimating a blood-glucose concentration in a patient from sensor measurements based, at least in part, on the estimated one or more parameters.

In at least one example implementation, the obtaining may further include: taking sensor measurements for the multiple blood glucose reference sample-sensor measurement pairs using at least one subcutaneous current sensor. In at least one other example implementation, the function may be defined at least partly by a slope and an offset. In at least one other example implementation, the one or more parameters may comprise a calfactor variable and an offset variable. In yet at least one other example implementation, a relationship between current sensor measurements corresponding to the blood glucose reference sample-sensor measurement pairs and sensor glucose concentration for the patient may be represented by a linear model, the linear model may be associated with a slope and an offset; and the slope and the offset of the linear model may be determinable from the calfactor variable and/or the offset variable.

In at least one other example implementation, the estimating may further include: estimating the one or more parameters using a linear Kalman filter estimator in which process noise and measurement noise are modeled as being constant. In at least one other example implementation, the estimating may further include: estimating the one or more parameters using a linear Kalman filter estimator in which process noise is adapted as a function of model performance. In at least one other example implementation, the estimating may further include: estimating the one or more parameters using a linear Kalman filter estimator in which measurement noise is adapted as a function of model performance. In at least one other example implementation, the estimating may further include: estimating the one or more parameters using a Bayesian estimator in which sensor measurements corresponding to the blood glucose reference sample-sensor measurement pairs may comprise an independent variable and blood glucose reference samples corresponding to the blood glucose reference sample-sensor measurement pairs may comprise a measured variable.

In at least one other example implementation, the method may further include: estimating a composite sensor glucose concentration value for the patient using multiple functions and at least one weighting factor that is derived from one or more quality indicators for multiple probability models.

In at least one other example implementation, the determining may further include determining multiple functions for estimating a blood-glucose concentration in the patient from sensor measurements; and the method may further include: estimating multiple sensor glucose concentration values for the patient using the multiple functions; the multiple functions associated with multiple probability models, which include the probability model; and determining a composite sensor glucose concentration value for the patient based, at least partly, on the multiple sensor glucose concentration values. In yet at least one other example implementation, the determining a composite sensor glucose concentration value for the patient may further include: weighting the multiple sensor glucose concentration values based, at least in part, on multiple quality indicators indicative of an accuracy of the multiple probability models. In yet at least one other example implementation, the multiple quality indicators may comprise multiple likelihood values; and the method may further include: calculating the multiple likelihood values based, at least partly, on error differences between sensor glucose concentration values estimated from the multiple probability models and reference blood glucose values from blood glucose reference samples.

In one or more example embodiments, an apparatus may include a calibration unit to receive one or more signals based on blood-glucose sensor measurements, the calibration unit may include one or more processors to: obtain multiple blood glucose reference sample-sensor measurement pairs; estimate one or more parameters of a probability model based, at least in part, on the blood glucose reference sample-sensor measurement pairs; and determine a function for estimating a blood-glucose concentration in a patient from sensor measurements based, at least in part, on the estimated one or more parameters.

In at least one example implementation, the calibration unit may be capable of obtaining the multiple blood glucose reference sample-sensor measurement pairs by: taking sensor measurements for the multiple blood glucose reference sample-sensor measurement pairs using at least one subcutaneous current sensor. In at least one other example implementation, the function may be defined at least partly by a slope and an offset.

In at least one other example implementation, the one or more parameters may comprise a calfactor variable and an offset variable. In yet at least one other example implementation, a relationship between current sensor measurements corresponding to the blood glucose reference sample-sensor measurement pairs and sensor glucose concentration for the patient may be represented by a linear model, and the linear model may be associated with a slope and an offset; and the slope and the offset of the linear model may be determinable from the calfactor variable and/or the offset variable.

In at least one other example implementation, the calibration unit may be capable of estimating the one or more parameters of a probability model by: estimating the one or more parameters using a linear Kalman filter estimator in which process noise and measurement noise are modeled as being constant. In at least one other example implementation, the calibration unit may be capable of estimating the one or more parameters of a probability model by: estimating the one or more parameters using a linear Kalman filter estimator in which process noise is adapted as a function of model performance. In at least one other example implementation, the calibration unit may be capable of estimating the one or more parameters of a probability model by: estimating the one or more parameters using a linear Kalman filter estimator in which measurement noise is adapted as a function of model performance.

In at least one other example implementation, the calibration unit may be capable of estimating the one or more parameters of a probability model by: estimating the one or more parameters using a Bayesian estimator in which sensor measurements corresponding to the blood glucose reference sample-sensor measurement pairs may comprise an independent variable and blood glucose reference samples corresponding to the blood glucose reference sample-sensor measurement pairs may comprise a measured variable. In at least one other example implementation, the one or more processors of the calibration unit may further be to: estimate a composite sensor glucose concentration value for the patient using multiple functions and at least one weighting factor that is derived from one or more quality indicators for multiple probability models.

In at least one other example implementation, the calibration unit may be capable of determining the function for estimating a blood-glucose concentration in the patient by determining multiple functions for estimating a blood-glucose concentration in the patient from sensor measurements; and the one or more processors of the calibration unit may further be to: estimate multiple sensor glucose concentration values for the patient using the multiple functions; the multiple functions associated with multiple probability models, which include the probability model; and determine a composite sensor glucose concentration value for the patient based, at least partly, on the multiple sensor glucose concentration values. In at least one other example implementation, the calibration unit may be capable of determining the composite sensor glucose concentration value for the patient by: weighting the multiple sensor glucose concentration values based, at least in part, on multiple quality indicators indicative of an accuracy of the multiple probability models. In at least one other example implementation, the multiple quality indicators may comprise multiple likelihood values; and the one or more processors of the calibration unit may further be to: calculate the multiple likelihood values based, at least partly, on error differences between sensor glucose concentration values estimated from the multiple probability models and reference blood glucose values from blood glucose reference samples.

In at least one other example implementation, the apparatus may further include: one or more blood-glucose sensors adapted to be coupled to the patient to obtain blood-glucose sensor measurements and adapted to provide the one or more signals based on the blood-glucose sensor measurements, the calibration unit may be capable of obtaining the multiple blood glucose reference sample-sensor measurement pairs via the one or more blood-glucose sensors using the one or more signals.

In one or more example embodiments, a system may include: means for obtaining multiple blood glucose reference sample-sensor measurement pairs; means for estimating one or more parameters of a probability model based, at least in part, on the blood glucose reference sample-sensor measurement pairs; and means for determining a function for estimating a blood-glucose concentration in a patient from sensor measurements based, at least in part, on the estimated one or more parameters.

In one or more example embodiments, an article may include at least one storage medium having stored thereon instructions executable by one or more processors to: obtain multiple blood glucose reference sample-sensor measurement pairs; estimate one or more parameters of a probability model based, at least in part, on the blood glucose reference sample-sensor measurement pairs; and determine a function for estimating a blood-glucose concentration in a patient from sensor measurements based, at least in part, on the estimated one or more parameters.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon the one or more signals generated by the sensor.

BRIEF DESCRIPTION OF THE FIGURES

Non-limiting and non-exhaustive features will be described with reference to the following figures, wherein like reference numerals refer to like parts throughout the various figures.

DETAILED DESCRIPTION

In an example glucose monitoring sensor and/or insulin delivery system environment, measurements reflecting blood-glucose levels may be employed in a closed loop infusion system for regulating a rate of fluid infusion into a body. In particular example embodiments, a sensor and/or system may be adapted to regulate a rate of insulin and/or glucagon infusion into a body of a patient based, at least in part, on a glucose concentration measurement taken from a body (e.g., from a blood-glucose sensor, including a current sensor). In certain example implementations, such a system may be designed to model a pancreatic beta cell (β-cell). Here, such a system may control an infusion device to release insulin into a body of a patient in an at least approximately similar concentration profile as might be created by fully functioning human β-cells if such were responding to changes in blood glucose concentrations in the body. Thus, such a closed loop infusion system may simulate a body's natural insulin response to blood glucose levels. Moreover, it may not only make efficient use of insulin, but it may also account for other bodily functions as well because insulin can have both metabolic and mitogenic effects.

According to certain embodiments, examples of closed-loop systems as described herein may be implemented in a hospital environment to monitor and/or control levels of glucose and/or insulin in a patient. Here, as part of a hospital or other medical facility procedure, a caretaker or attendant may be tasked with interacting with a closed-loop system to, for example: enter blood-glucose reference measurement samples into control equipment to calibrate blood glucose measurements obtained from blood-glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose and/or insulin in a patient. Here, a patient or other non-medical professional may be responsible for interacting with a closed-loop system.

Figure 1:
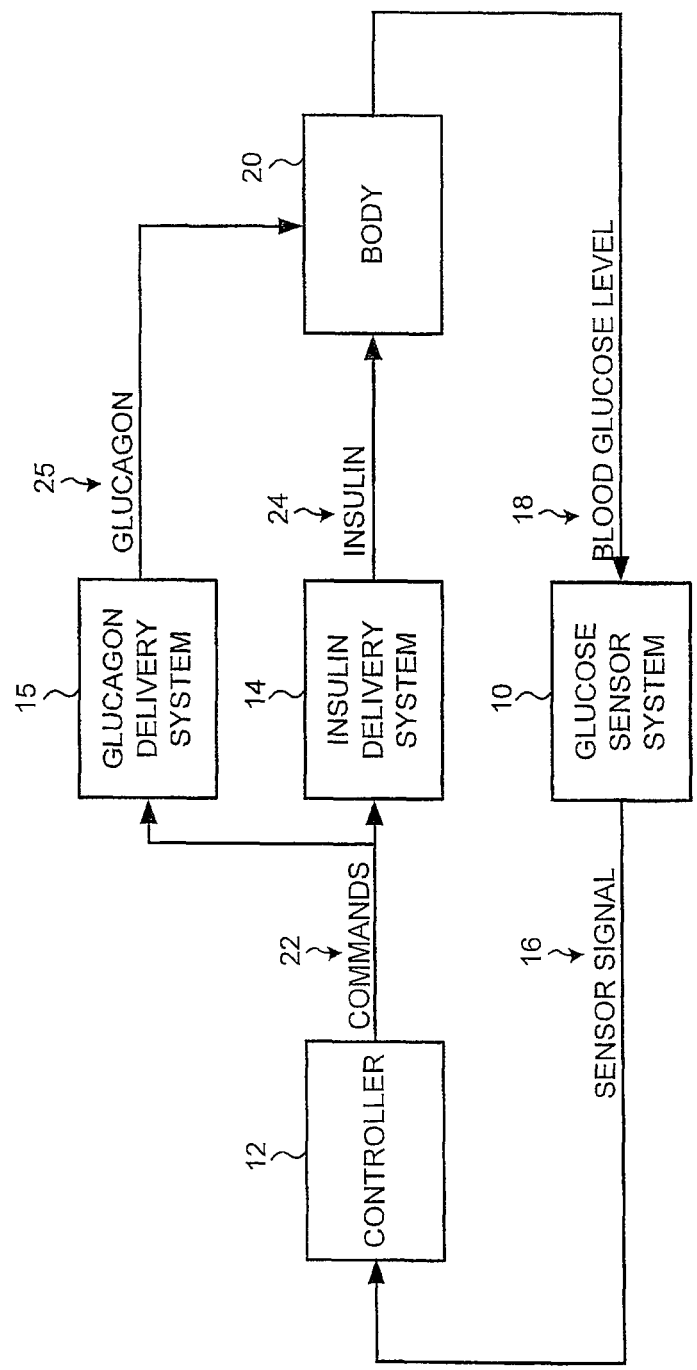
FIG. 1 is a block diagram of an example closed loop glucose control system in accordance with an embodiment.

FIG. 1 is a block diagram of an example closed loop glucose control system in accordance with an embodiment. Particular embodiments may include a glucose sensor system 10, a controller 12, an insulin delivery system 14, and a glucagon delivery system 15, as shown in FIG. 1. In certain example embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14 and/or glucagon delivery system 15. Insulin delivery system 14 may receive commands 22 and infuse insulin 24 into body 20 in response to commands 22. Likewise, glucagon delivery system 15 may receive commands 22 and infuse glucagon 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system.

Controller 12 may include electrical components and software to generate commands 22 for insulin delivery system 14 and/or glucagon delivery system 15 based on sensor signal 16. Controller 12 may also include a controller communication system to receive sensor signal 16 and provide commands 22 to insulin delivery system 14 and/or glucagon delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 15 may include an infusion device and/or an infusion tube to infuse glucagon 25 into body 20. In alternative embodiments, insulin 24 and glucagon 25 may be infused into body 20 using a shared infusion tube. In other alternative embodiments, insulin 24 and/or glucagon 25 may be infused using an intravenous system for providing fluids to a patient (e.g., in a hospital or other medical environment). When an intravenous system is employed, glucose may be infused directly into a bloodstream of a body instead of or in addition to infusing glucagon into interstitial tissue. It should be understood, however, that certain example embodiments may include an insulin delivery system 14, such as an insulin delivery system without a glucagon delivery system.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Overview of Example Systems

Figure 2:
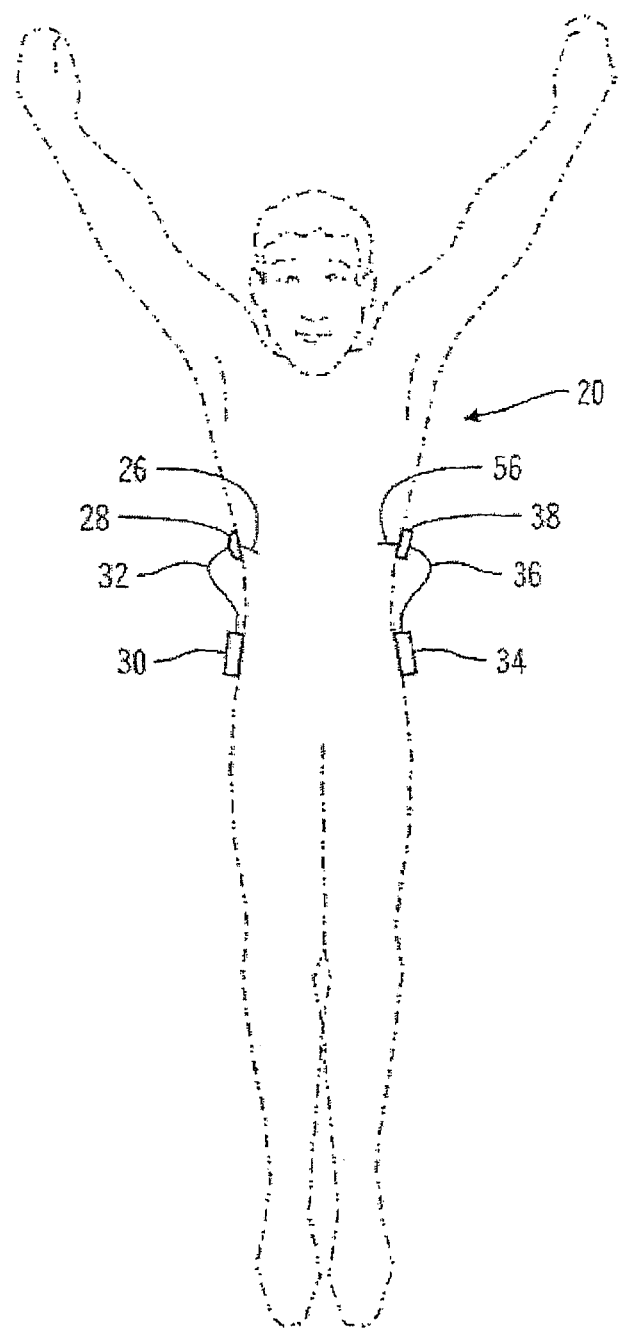
FIG. 2 is a front view of example closed loop hardware located on a body in accordance with an embodiment.
Figure 3:
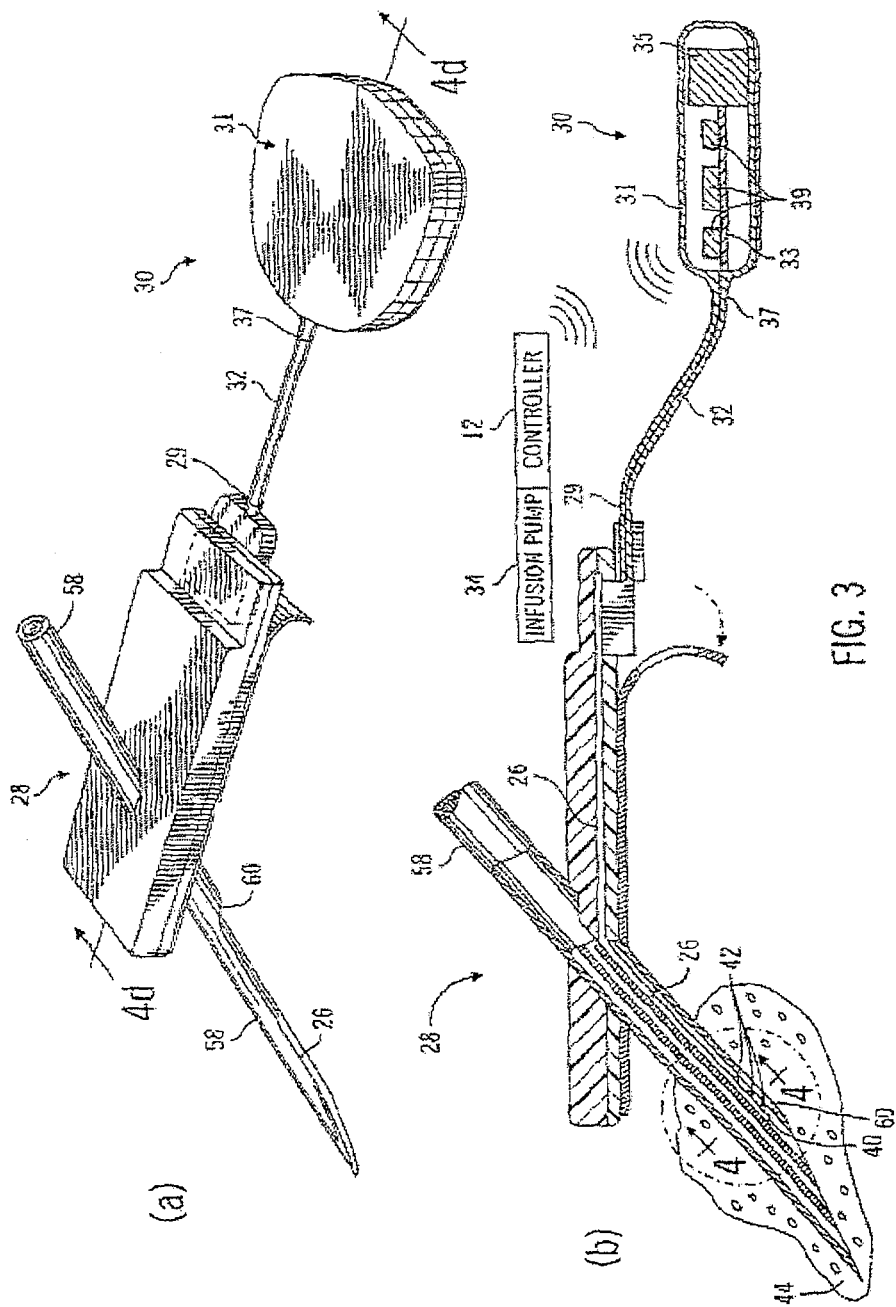
FIG. 3(a) is a perspective view of an example glucose sensor system for use in accordance with an embodiment.
FIG. 3(b) is a side cross-sectional view of a glucose sensor system of FIG. 3(a) for an embodiment.
FIG. 3(c) is a perspective view of an example sensor set of a glucose sensor system of FIG. 3(a) for an embodiment.
FIG. 3(d) is a side cross-sectional view of a sensor set of FIG. 3(c) for an embodiment.
Figure 3:
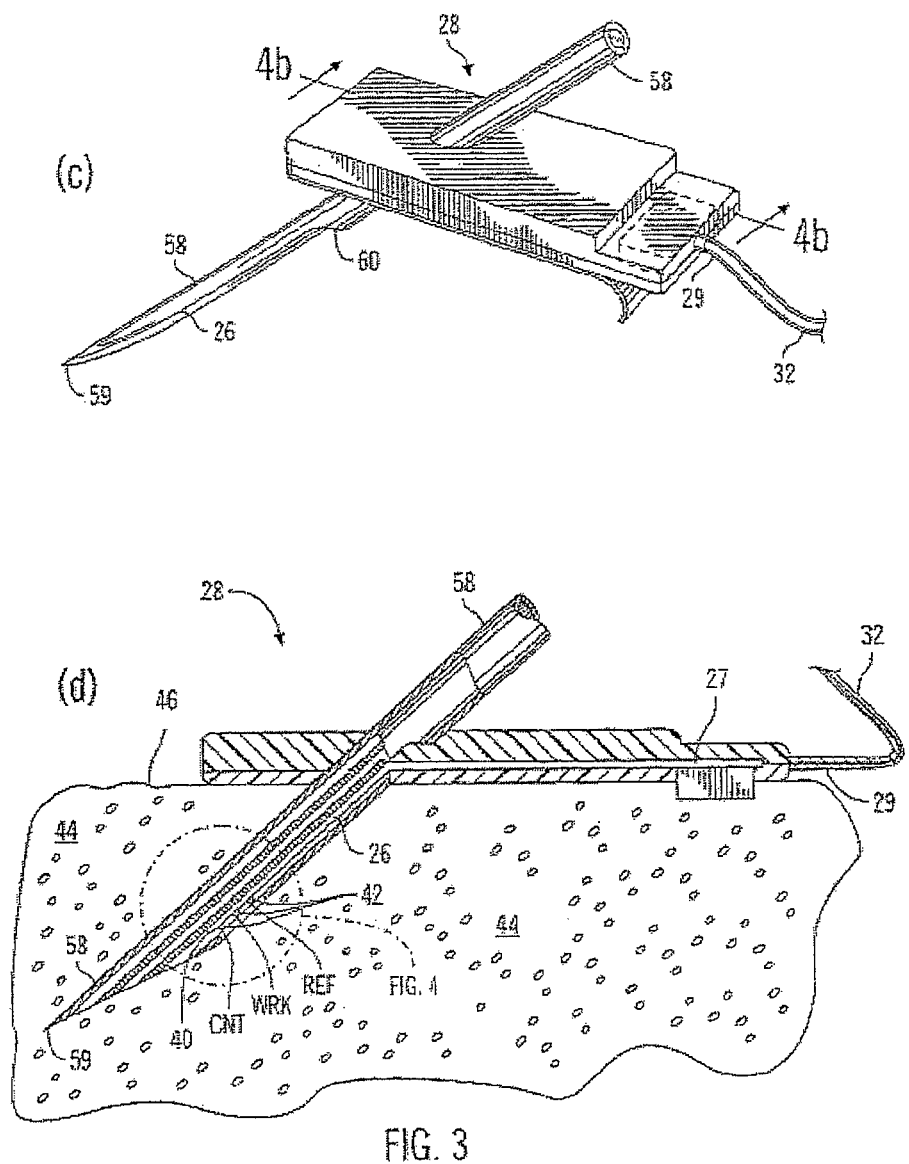
Figure 4:
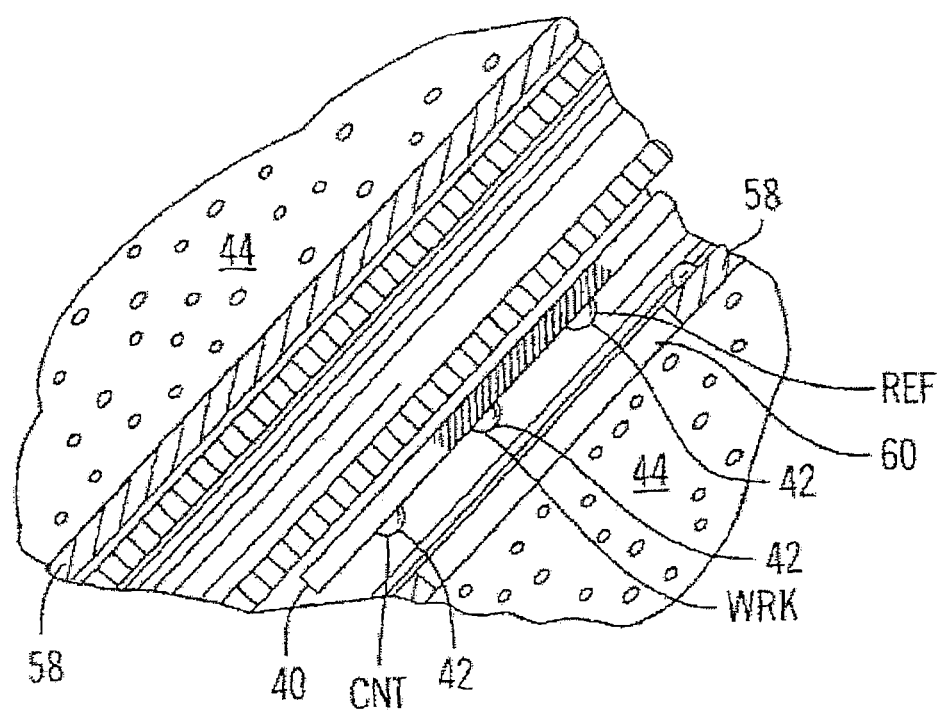
FIG. 4 is a cross sectional view of an example sensing end of a sensor set of FIG. 3(d) for an embodiment.
Figure 5:
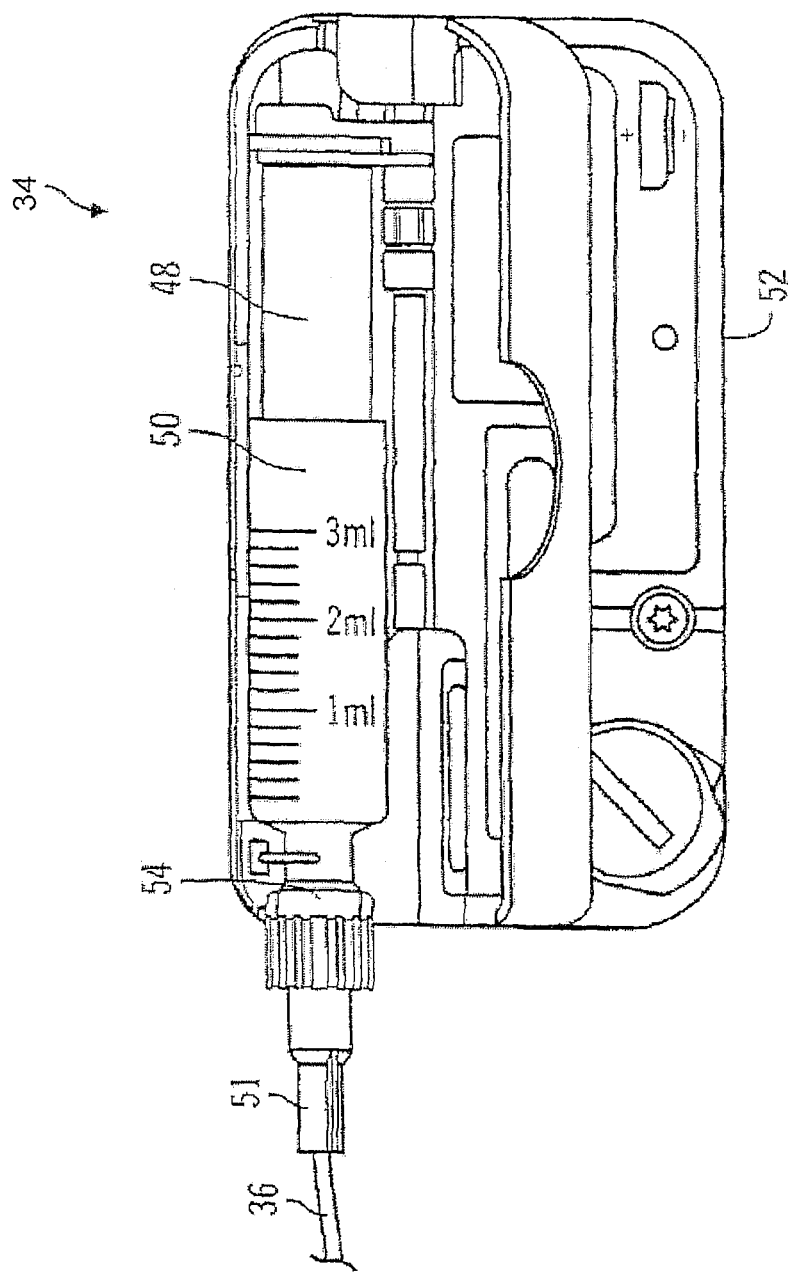
FIG. 5 is a top view of an example infusion device with a reservoir door in an open position, for use according to an embodiment.
Figure 6:
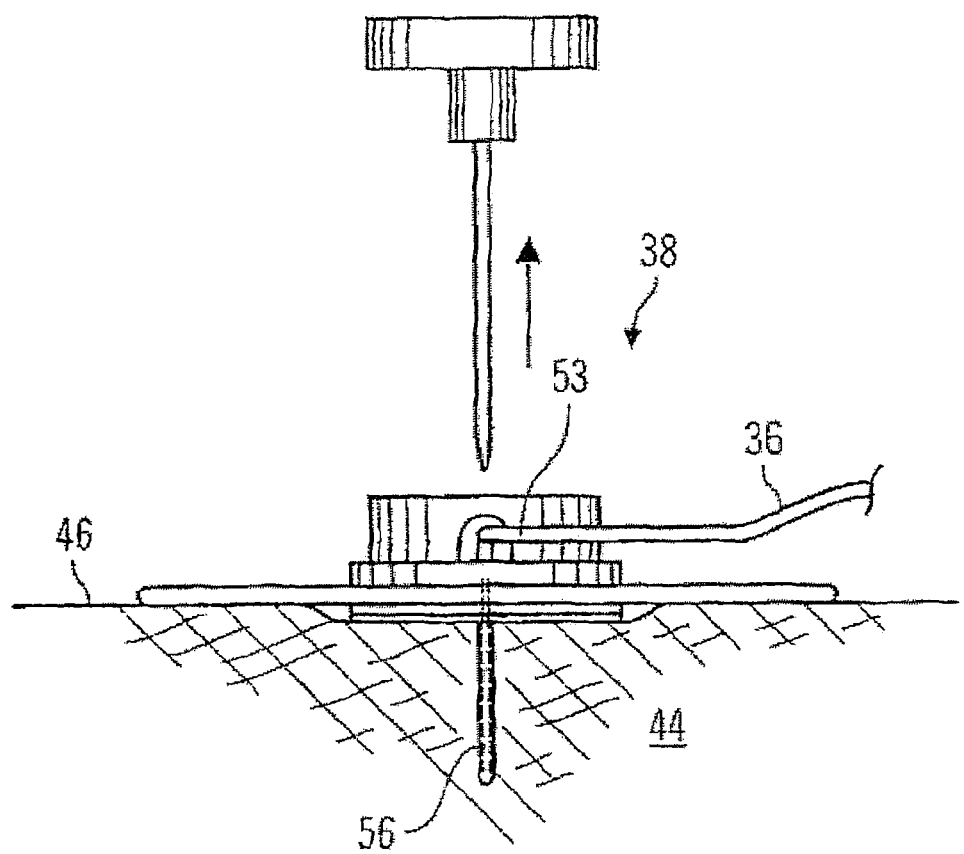
FIG. 6 is a side view of an example infusion set with an insertion needle pulled out, for use according to an embodiment.

FIGS. 2-6 illustrate example glucose control systems in accordance with certain embodiments. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggybacks off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example System and/or Environmental Delays

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal.

Figure 7:
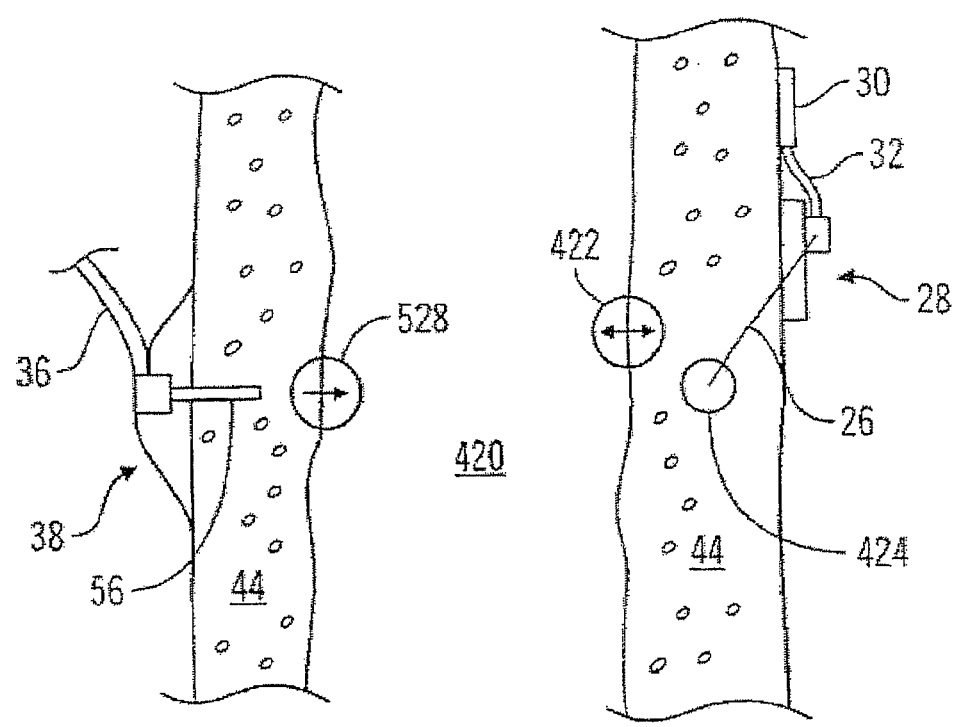
FIG. 7 is a cross-sectional view of an example sensor set and an example infusion set attached to a body in accordance with an embodiment.

FIG. 7 is a cross-sectional view of an example sensor set and an example infusion set that is attached to a body in accordance with an embodiment. In particular example implementations, as shown in FIG. 7, a physiological delay may arise from a time that transpires while glucose moves between blood plasma 420 and interstitial fluid (ISF). This example delay may be represented by a circled double-headed arrow 422. As discussed above with reference to FIG. 2-6, a sensor may be inserted into subcutaneous tissue 44 of body 20 such that electrode(s) 42 (e.g., of FIGS. 3 and 4) near a tip, or sending end 40, of sensor 26 are in contact with ISF. However, a parameter to be measured may include a concentration of glucose in blood.

Glucose may be carried throughout a body in blood plasma 420. Through a process of diffusion, glucose may move from blood plasma 420 into ISF of subcutaneous tissue 44 and vice versa. As blood glucose level 18 (e.g., of FIG. 1) changes, so does a glucose level of ISF. However, a glucose level of ISF may lag behind blood glucose level 18 due to a time required for a body to achieve glucose concentration equilibrium between blood plasma 420 and ISF. Some studies have shown that glucose lag times between blood plasma and ISF may vary between, e.g., 0 to 30 minutes. Some parameters may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 7. Sensor electrodes 42 (e.g., of FIGS. 3 and 4) may be coated with protective membranes that keep electrodes 42 wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Thus, an insulin delivery delay may be caused by a diffusion delay, which may be a time for insulin that has been infused into a tissue to diffuse into the blood stream. Other contributors to insulin delivery delay may include, but are not limited to: a time for a delivery system to deliver insulin to a body after receiving a command to infuse insulin; a time for insulin to spread throughout a circulatory system once it has entered the blood stream; and/or by other mechanical, electrical/electronic, or physiological causes alone or in combination, just to name a few examples. In addition, a body clears insulin even while an insulin dose is being delivered from an insulin delivery system into the body. Because insulin is continuously cleared from blood plasma by a body, an insulin dose that is delivered to blood plasma too slowly or is delayed is at least partially, and possibly significantly, cleared before the entire insulin dose fully reaches blood plasma. Therefore, an insulin concentration profile in blood plasma may never achieve a given peak (nor follow a given profile) that it may have achieved if there were no delay.

Moreover, there may also be a processing delay as an analog sensor signal Isig is converted to digital sensor values Dsig. In particular example embodiments, an analog sensor signal Isig may be integrated over one-minute intervals and converted to a number of counts. Thus, in such a case, an analog-to-digital (A/D) conversion time may result in an average delay of 30 seconds. In particular example embodiments, one-minute values may be averaged into 5-minute values before they are provided to controller 12 (e.g., of FIG. 1). A resulting average delay may be two-and-one-half minutes (e.g., half of the averaging interval). In example alternative embodiments, longer or shorter integration times may be used that result in longer or shorter delay times.

In other example embodiments, an analog sensor signal current Isig may be continuously converted to an analog voltage Vsig, and an A/D converter may sample voltage Vsig every 10 seconds. Thus, in such a case, six 10-second values may be pre-filtered and averaged to create a one-minute value. Also, five one-minute values may be filtered and averaged to create a five-minute value that results in an average delay of two-and-one-half minutes. In other alternative embodiments, other sensor signals from other types of sensors may be converted to digital sensor values Dsig as appropriate before transmitting the digital sensor values Dsig to another device. Moreover, other embodiments may use other electrical components, other sampling rates, other conversions, other delay periods, a combination thereof, and so forth.

System Configuration Examples

FIG. 8(a)-8(d) illustrate example diagrams of one or more devices and their components for glucose control systems in accordance with certain embodiments. These FIG. 8(a)-8(d) show exemplary, but not limiting, illustrations of components that may be utilized with certain controller(s) that are described herein above. Various changes in components, layouts of such components, combinations of elements, and so forth may be made without departing from the scope of claimed subject matter.

Before it is provided as an input to controller 12 (e.g., of FIG. 1), a sensor signal 16 may be subjected to signal conditioning such as pre-filtering, filtering, calibrating, and so forth, just to name a few examples. Components such as a pre-filter, one or more filters, a calibrator, controller 12, etc. may be separately partitioned or physically located together (e.g., as shown in FIG. 8(a)), and they may be included with a telemetered characteristic monitor transmitter 30, an infusion device 34, a supplemental device, and so forth.

In particular example embodiments, a pre-filter, filter(s), and a calibrator may be included as part of telemetered characteristic monitor transmitter 30, and a controller (e.g., controller 12) may be included with infusion device 34, as shown in FIG. 8(b). In example alternative embodiments, a pre-filter may be included with telemetered characteristic monitor transmitter 30, and a filter and calibrator may be included with a controller in an infusion device, as shown in FIG. 8(c). In other alternative example embodiments, a pre-filter may be included with telemetered characteristic monitor transmitter 30, while filter(s) and a calibrator are included in supplemental device 41, and a controller may be included in the infusion device, as shown in FIG. 8(d).

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

Figure 8:
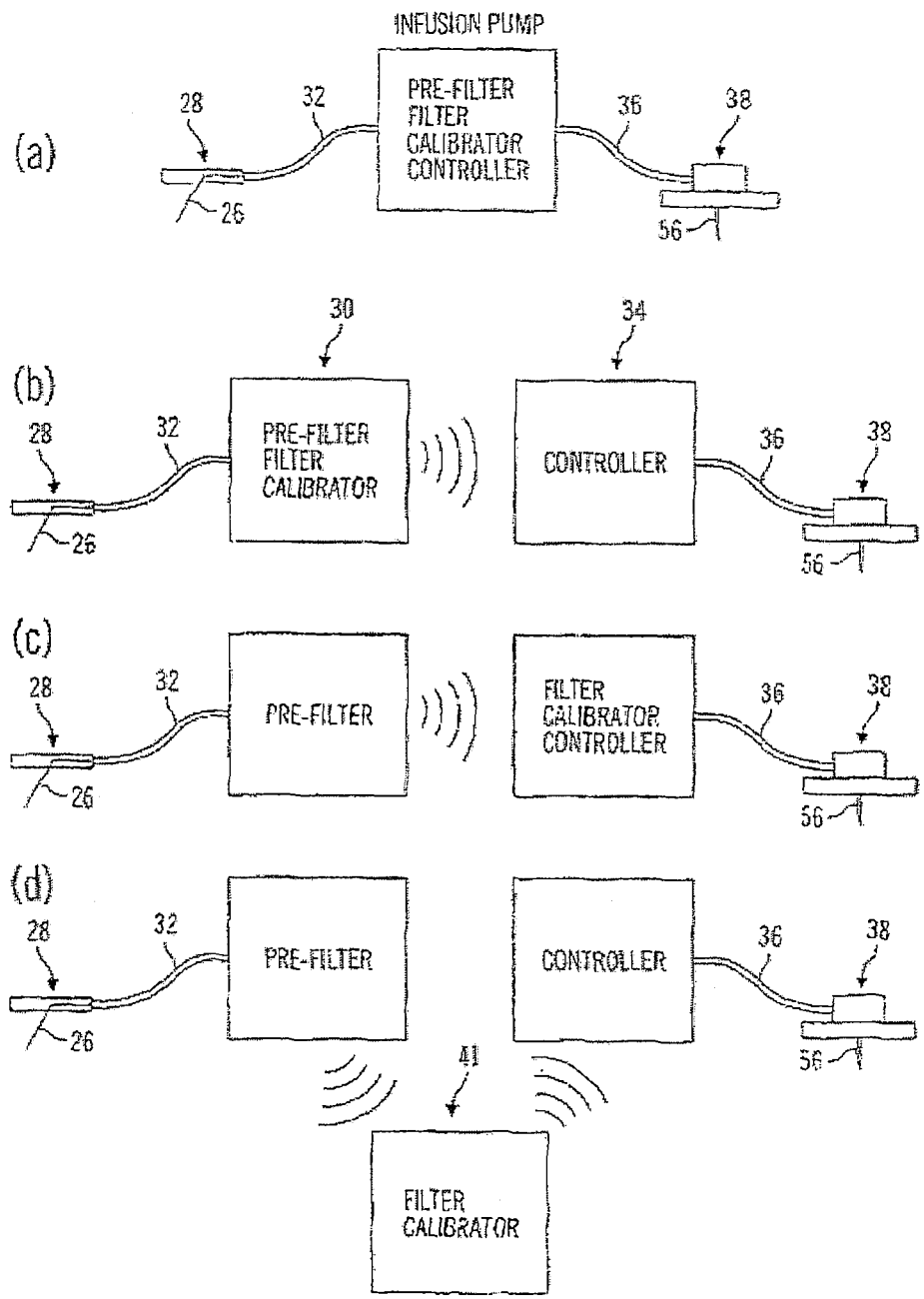
FIG. 8(a) is a diagram of an example single device and its components for a glucose control system in accordance with an embodiment.
FIG. 8(b) is a diagram of two example devices and their components for a glucose control system in accordance with an embodiment.
FIG. 8(c) is another diagram of two example devices and their components for a glucose control system in accordance with an embodiment.
FIG. 8(d) is a diagram of three example devices and their components for a glucose control system in accordance with an embodiment.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator. In alternative example embodiments, more, fewer, and/or different components may be implemented than those that are shown in FIG. 8 and/or described herein above.

In particular example embodiments, RF telemetry may be used to communicate between devices that contain one or more components, such as telemetered characteristic monitor transmitter 30 and infusion device 34. In alternative example embodiments, other communication mediums may be employed between devices, such as wireless wide area network (WAN) (e.g., cell communication), Wi-Fi, wires, cables, IR signals, laser signals, fiber optics, ultrasonic signals, and so forth, just to name a few examples.

Example Approaches to Calibrating Glucose and/or Insulin Systems

Figure 9:
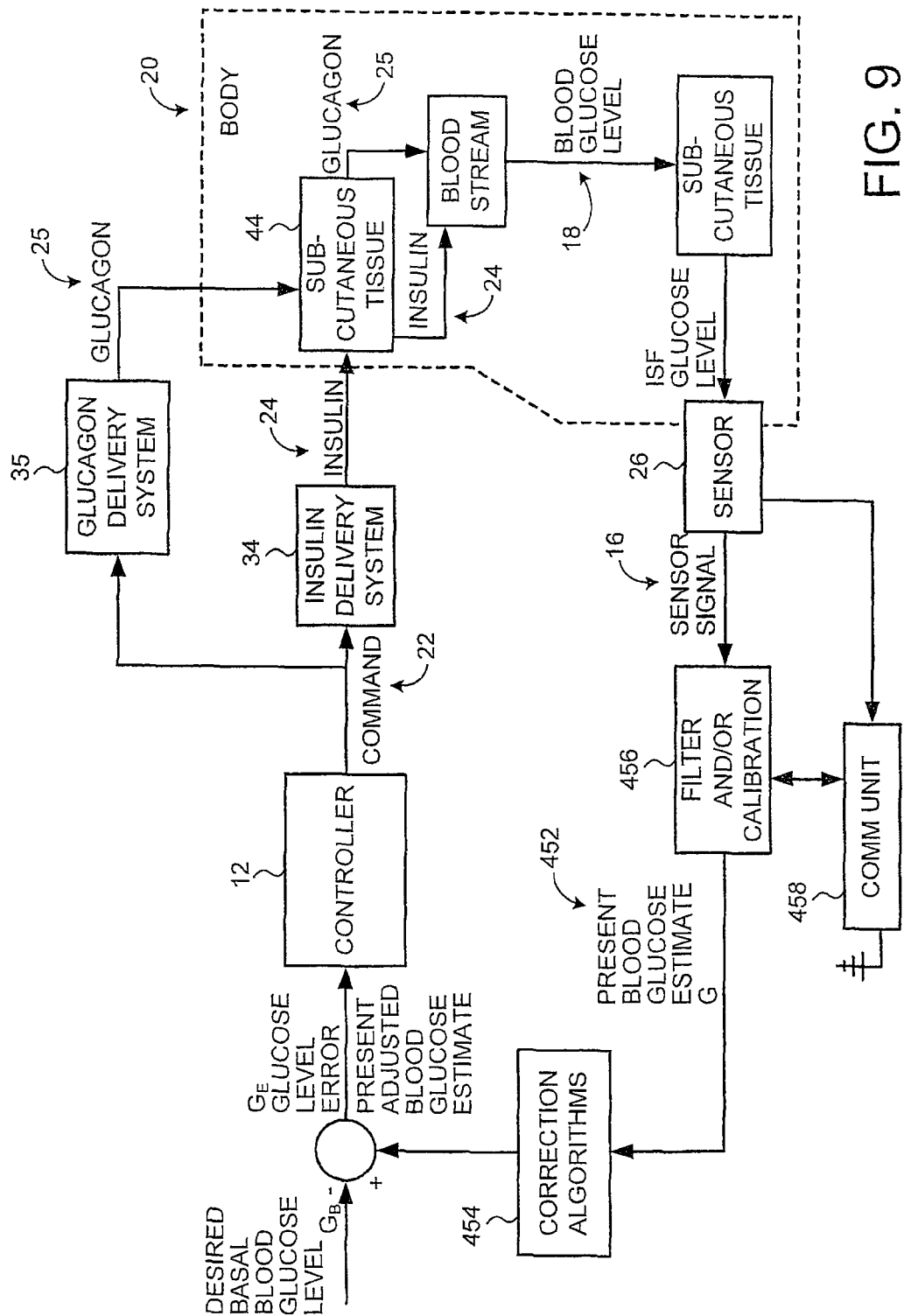
FIG. 9 is a block diagram of an example closed loop system to control blood glucose levels using a controller, a filter and/or calibration unit, and/or correction algorithms through insulin infusion based on glucose level feedback in accordance with an embodiment.

FIG. 9 is a block diagram of an example closed loop system to control blood glucose levels using a controller, a filter and/or calibration unit, and/or correction algorithms through insulin infusion based on glucose level feedback in accordance with an embodiment. In particular example embodiments, a closed loop control system may be used for delivering insulin to a body to compensate for β-cells that perform inadequately. There may be a desired basal blood glucose level $G_B$ for a particular body. A difference between a desired basal blood glucose level $G_B$ and an estimate of a present blood glucose level G is the glucose level error $G_E$ that may be corrected. For particular example embodiments, glucose level error $G_E$ may be provided as an input to controller 12, as shown in FIG. 9. Although controller 12 may be realized as a proportional-integral-derivative (PID) controller, claimed subject matter is not so limited, and controller 12 may be realized in alternative manners.

If glucose level error $G_E$ is positive (meaning, e.g., that a present estimate of blood glucose level G is higher than a desired basal blood glucose level $G_B$), then a command from controller 12 may generate a command 22 to drive insulin delivery system 34 to provide insulin 24 to body 20. Insulin delivery system 34 may be an example implementation of insulin delivery system 14 (e.g., of FIG. 1). Likewise, if $G_E$ is negative (meaning, e.g., that a present estimate of blood glucose level G is lower than a desired basal blood glucose level $G_B$), then a command from controller 12 may generate a command 22 to drive glucagon delivery system 35 to provide glucagon 25 to body 20. Glucagon delivery system 35 may be an example implementation of glucagon delivery system 15 (e.g., of FIG. 1).

Figure 10:
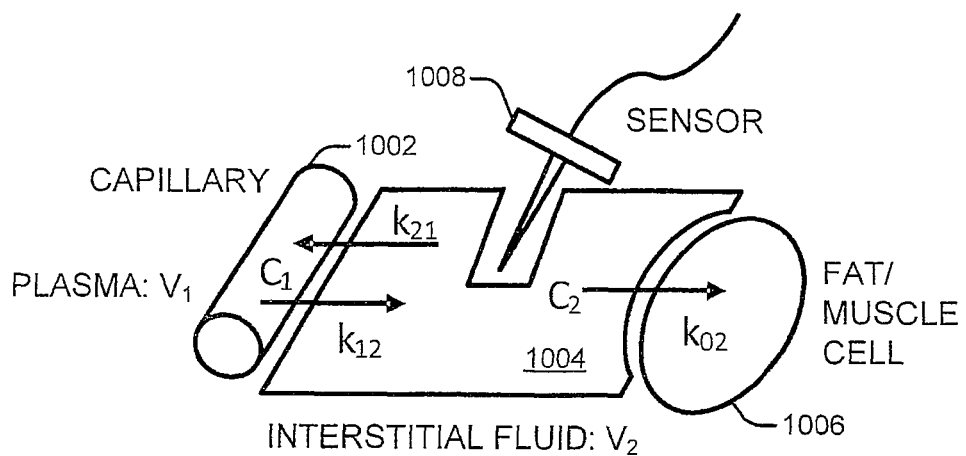
FIG. 10(a) is a schematic diagram that illustrates an example of glucose propagation within tissues of a body in conjunction with a sensor in accordance with an embodiment.
FIG. 10(b) is a graphical diagram that illustrates an example relationship between glucose that is present in blood and glucose that is present within interstitial fluid in accordance with an embodiment.
Figure 10:
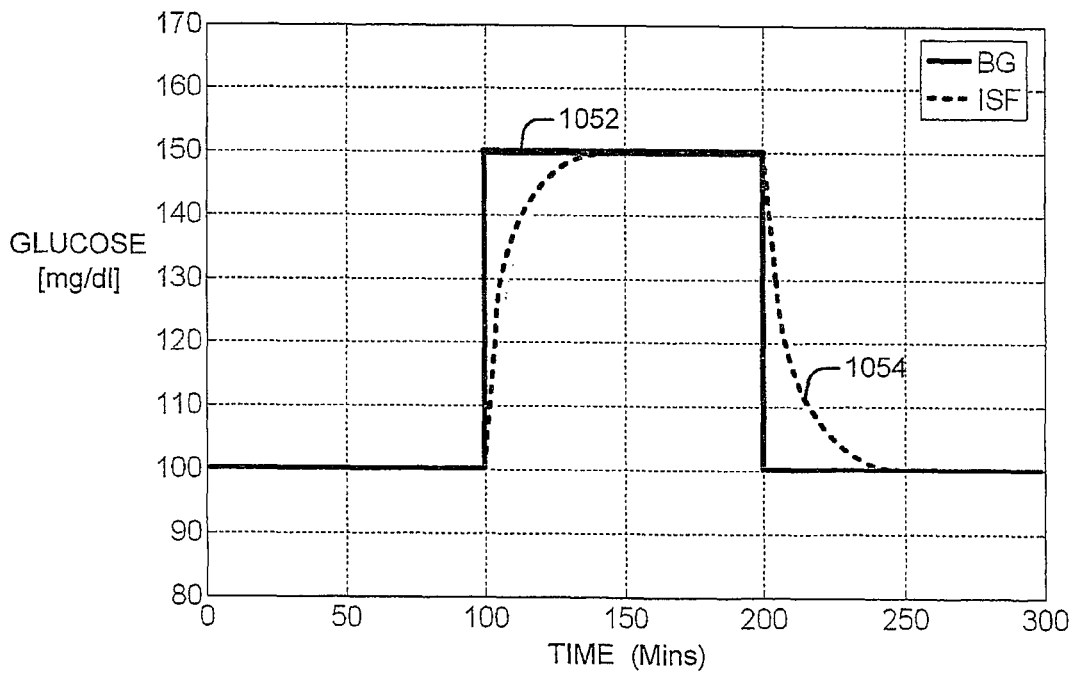

In terms of a control loop for purposes of discussion, glucose may be considered to be positive, and therefore insulin may be considered to be negative. Sensor 26 may sense an ISF glucose level of body 20 and generate a sensor signal 16. For certain example embodiments, a control loop may include a filter and/or calibration unit 456 and/or correction algorithm(s) 454. However, this is by way of example only, and claimed subject matter is not so limited. Sensor signal 16 may be filtered/or and calibrated at unit 456 to create an estimate of present blood glucose level 452. In certain example embodiments that are described herein with particular reference to FIGS. 10(*a*)-21, filtering and/or calibrating may be performed by filter and/or calibration unit 456. Although shown separately, filter and/or calibration unit 456 may be integrated with controller 12 without departing from claimed subject matter. Moreover, filter and/or calibration unit 456 may alternatively be realized as part of controller 12 (or vice versa) without departing from claimed subject matter.

In particular example embodiments, an estimate of present blood glucose level G may be adjusted with correction algorithms 454 before it is compared to a desired basal blood glucose level $G_8$ to calculate a new glucose level error $G_E$ to start a loop again. Also, an attendant, a caretaker, a patient, etc. may obtain blood glucose reference sample measurements from a patient's blood using, e.g., glucose test strips. These blood-based sample measurements may be used to calibrate ISF-based sensor measurements using techniques, e.g., such as those described in U.S. Pat. No. 6,895,263, issued 17 May 2005, separately or in conjunction with the (e.g., calibration-related) principles that are described herein.

For an example PID-type of controller 12, if a glucose level error $G_E$ is negative (meaning, e.g., that a present estimate of blood glucose level is lower than a desired basal blood glucose level $G_B$), then controller 12 may reduce or stop insulin delivery depending on whether an integral component response of a glucose error $G_E$ is still positive. In alternative embodiments, as discussed below, controller 12 may initiate infusion of glucagon 25 if glucose level error $G_E$ is negative. If a glucose level error $G_E$ is zero (meaning, e.g., that a present estimate of blood glucose level is equal to a desired basal blood glucose level $G_B$), then controller 12 may or may not issue commands to infuse insulin 24 or glucagon 25, depending on a derivative component (e.g., whether glucose level is raising or falling) and/or an integral component (e.g., how long and by how much glucose level has been above or below basal blood glucose level $G_B$).

To more clearly understand the effects that a body has on such a control loop, a more detailed description of physiological effects that insulin has on glucose concentration in ISF is provided. In particular example embodiments, infusion delivery system 34 delivers insulin into ISF of subcutaneous tissue 44 (e.g., also of FIGS. 3, 4, and 6) of body 20. Alternatively, insulin delivery system 34 or a separate infusion device (e.g., glucagon delivery system 35) may similarly deliver glucose into ISF of subcutaneous tissue 44. Here, insulin may diffuse from local ISF surrounding a cannula into blood plasma and spread throughout body 20 in a main circulatory system. Infused insulin may diffuse from blood plasma into ISF substantially throughout the entire body.

Here in the body, insulin 24 may bind with and activate membrane receptor proteins on cells of body tissues. This may facilitate glucose permeation into activated cells. In this way, tissues of body 20 may take up glucose from ISF. As ISF glucose level decreases, glucose may diffuse from blood plasma into ISF to maintain glucose concentration equilibrium. Glucose in ISF may permeate a sensor membrane of sensor 26 and affect sensor signal 16. Propagation of glucose throughout a body is described further herein below with particular reference to FIG. 10(*a*).

In addition, insulin may have direct and indirect effects on liver glucose production. Typically, increased insulin concentration may decrease liver glucose production. Therefore, acute and immediate insulin response may not only help a body to efficiently take up glucose, but it may also substantially stop a liver from adding to glucose in the blood stream.

In alternative example embodiments, as pointed out above, insulin and/or glucose may be delivered more directly into the blood stream instead of into ISF, such as by delivery into veins, arteries, the peritoneal cavity, and so forth, just to name a few examples. Accordingly, any time delay associated with moving insulin and/or glucose from ISF into blood plasma may be diminished. In other alternative example embodiments, a glucose sensor may be in contact with blood or other body fluids instead of ISF, or a glucose sensor may be outside of a body such that it may measure glucose through a non-invasive means. Embodiments using alternative glucose sensors may have shorter or longer delays between an actual blood glucose level and a measured blood glucose level.

One or more controller gains may be selected so that commands from a controller 12 direct infusion device 34 to release insulin 24 into body 20 at a particular rate. Such a particular rate may cause insulin concentration in blood to follow a similar concentration profile as would be caused by fully functioning human β-cells responding to blood glucose concentrations in a body. Similarly, controller gain(s) may be selected so that commands from controller 12 direct infusion device 35 to release glucagon 25 in response to insulin excursions. In particular example embodiments, controller gains may be selected at least partially by observing insulin response(s) of several normal glucose tolerant (NGT) individuals having healthy, normally-functioning β-cells.

In one or more example implementations, a system may additionally include a communication unit 458. A communication unit 458 may comprise, by way of example but not limitation, a wireless wide area communication module (e.g., a cell modem), a transmitter and/or a receiver (e.g., a transceiver), a Wi-Fi chip or radio, some combination thereof, and so forth. Communication unit 458 may receive signals from filter and/or calibration unit 456 and/or from sensor 26 (e.g., sensor signal 16). Although not specifically shown in FIG. 9, communication unit 458 may also receive signals from other units (e.g., controller 12). Also, communication unit 458 may be capable of providing signals to any of the other units of FIG. 9 (e.g., controller 12, filter and/or calibration unit 456, etc.). Communication unit 458 may also be integrated with or otherwise form a part of another unit, such as controller 12 or filter and/or calibration unit 456.

Communication unit 458 may be capable of transmitting calibration output, calibration failure alarms, control algorithms state, and other physiological, hardware, and/or software data (e.g., diagnostic data), etc. to a remote data center for additional processing and/or storage (e.g., for remote telemetry purposes). These transmissions can be performed automatically, semi-automatically (e.g., at the request of the remote data center), and/or manually at the request of the patient, and so forth, just to provide a few examples. The data can be subsequently served on request to remote clients including, but not limited to, mobile phones, physician's workstations, patient's desktop computers, any combination of the above, and so forth, just to name a few examples. Communication unit 458 may also be capable of receiving from a remote location various information, including but not limited to: calibration information, instructions, other control information, some combination thereof, and so forth. Such control information may be provided from communication unit 458 to other system unit(s) (e.g., controller 12, filter and/or calibration unit 456, etc.).

A glucose and/or insulin control system may be calibrated relatively constantly, at intervals, regularly, occasionally, upon request, at other specified or random times, some combination thereof, and so forth. A continuous glucose measuring sensor (CGMS), for example, may detect a glucose concentration in ISF and transmit a proportional current signal. A current signal (isig) may be linearly correlated with a reference blood glucose concentration (BG). Hence, a linear model, with two parameters (e.g., slope and offset), may be used to calculate a sensor glucose concentration (SG) from sensor current isig. In order to accurately measure SG, parameters of such a linear model may be periodically calibrated by obtaining BG sample measurements via a BG meter or YSI.

Calibration may be performed by employing, for example, any one or more of multiple techniques. Five different example techniques are described below. First, a Bayesian (B) method that uses a Moving Chain Monte Carlo (MCMC) algorithm may be employed. This is a relatively robust technique, especially if/when significant process and/or measurement noises are present. However, an MCMC algorithm is typically relatively more computationally intensive. A second technique may use a linear Kalman Filter (KF). A KF technique may be relatively accurate in estimating model parameters, and it is also usually less computationally intensive than a Bayesian method. However, a KF technique may reflect measurement noise more in estimated parameters.

A third technique may use a linear Kalman Filter with an adaptive process noise matrix (KFQ). Unlike a KF technique, a KFQ method may update a process noise matrix proportional to a bias (e.g., a difference between an estimated value and a true or reference value) of the model if/when a BG sample measurement is available. Therefore, when a bias is large, the gains calculated by KFQ in order to update model parameters are likely to be more conservative (e.g., smaller). Hence, parameters can be updated proportionally based on the performance of the model. A fourth technique may use a linear Kalman Filter with an adaptive measurement noise matrix (KFR). Unlike a KF technique, a KFR method may update a measurement noise matrix proportional to an error between an estimated value and a true value. Like a KFQ technique, when an error is large, gains calculated by KFR in order to update model parameters may be more conservative. A fifth technique may include estimating one or more parameters using a linear Kalman Filter in which both process noise and measurement noise are adapted as a function of model performance. Any two or more, all five of these, and/or other techniques may be used in parallel. If used in parallel, a weighting scheme may be assigned to each technique based on its respective performance. Based on the weights, a combined SG value may be calculated from two or more of the five example methods. These five techniques are described herein below with particular reference to FIGS. 19-21. Although five methods are described herein by way of example, claimed subject matter is not so limited, and other technique(s) may alternatively be implemented.

As is described herein above with particular reference to FIG. 7 and further herein below with particular reference to FIG. 10(a), there is typically a time lag between blood glucose and interstitial fluid (ISF) glucose. Such a time lag can decrease an accuracy of real-time continuous glucose monitoring (CGM) systems that use subcutaneous sensors (or other sensors that do not directly sense glucose in the blood). Each ISF glucose value measured in real-time may be lagging blood glucose (BG) by the sum of this time lag plus any inherent electrochemical sensor delay due to the reaction process, as well as any front-end signal processing delays incurred to produce smooth traces. Furthermore, this time lag can create ambiguity in a sensor calibration process because this lag can appear as an offset normally attributed to background current.

Accurately correcting for this time lag can improve overall performance, and it can potentially at least reduce sources of variance incurred while calibrating, especially on fast rising and/or falling glucose excursions. Such time lag correction can also provide a user with a relatively instantaneous BG values with latent periods removed. This can be particularly relevant in the context of closed loop devices in which insulin infusions may be changed relatively frequently (e.g., on a per minute basis).

For particular example implementations(s), algorithms are described that include an inverse filter with noise reduction properties, which is known as a Wiener filter, to correct for a determinable time lag while performing a degree of smoothing. Certain example embodiments may calculate a time delay between ISF glucose and plasma glucose, measure a noise level of a sensor signal, and/or use these two components to develop in real-time a time lag correction and noise reduction filter. A filter residual may be calibrated using any of a number of algorithms (e.g., linear regression, etc.).

Example dynamics for plasma and ISF glucose are described with reference to FIG. 10(a). More specifically, an example two compartment model is illustrated in FIG. 10(a). It may be used to represent a dynamic relationship between ISF glucose and plasma glucose. FIG. 10(a) is a schematic diagram 1000 that illustrates an example of glucose propagation within tissues of a body in conjunction with a sensor in accordance with an embodiment. FIG. 10(a) also relates to FIG. 7, which is described herein above.

Diagram 1000 includes a capillary 1002 (or, more generally, a blood vessel), ISF 1004, and a fat and/or muscle cell 1006. With reference to FIG. 9, these portions may relate to body 20. More specifically, capillary 1002 (e.g., which may contain blood plasma 420 of FIG. 7) may correspond to a blood stream, and ISF 1004 may correspond to, for example, subcutaneous tissue 44 (e.g., of FIGS. 7 and 9). Diagram 1000 also includes a sensor 1008. Sensor 1008 may correspond to sensor 26 (e.g., of FIGS. 7 and 9). Although shown in FIG. 10(a) and generally described herein as a subcutaneous current sensor placed within ISF, sensor 1008 may alternatively indirectly sense blood glucose from another portion of a body without departing from claimed subject matter. Plasma of capillary 1002 has a volume of $V_1$. ISF 1004 has a volume of $V_2$. Diagram 1000 further indicates two concentrations $C_1$ and $C_2$ and three rates of propagation $k_{02}$, $k_{12}$, and $k_{21}$.

A two compartment model is based on an assumption, without loss of generality or limitation, that a capillary 1002 separating plasma and ISF 1004 compartments creates a resistance to glucose diffusion from plasma space into ISF space. Glucose may be cleared from ISF space by a rate proportional to, for example, a concentration of glucose in that compartment. An example mathematical relationship is represented by the following mass balance equation:

$$\frac{dC_2}{dt} = -(k_{02} + k_{12})C_2 + k_{21}\frac{V_1}{V_2}C_1 \qquad (1)$$

where a rate of glucose clearance from subcutaneous tissue has a constant uptake rate of $k_{02}$, and constant glucose diffusion rates between plasma and subcutaneous tissue of $k_{12}$ and $k_{21}$, respectively. Plasma and ISF compartments have concentrations $C_1$ and $C_2$ and corresponding volumes $V_1$ and $V_2$, respectively.

A plasma-to-ISF time constant and gradient can be expressed as $$\frac{C_2}{C_1} = \frac{k_{21}}{k_{12} + k_{02}} \cdot \frac{V_1}{V_2}, \quad \tau = \frac{1}{k_{12} + k_{02}} \quad (2)$$

where time constant $\tau$ is the time delay between plasma and ISF glucose. Equation (2) assumes, without loss of generality or limitation, steady state conditions in which a steady state glucose concentration in an ISF compartment ($C_2$) may be dependent upon a rate of glucose clearance from this compartment ($k_{02}$) and a rate of glucose diffusion to the compartment ($k_{12}$ and $k_{21}$). Rate parameters are assumed, without loss of generality or limitation, to be constant; consequently, a time lag between ISF glucose and plasma glucose concentration may also be constant, as well may be the gradient thereof too.

FIG. 10(b) is a graphical diagram 1050 that illustrates an example relationship between glucose that is present in blood and glucose that is present within ISF in accordance with an embodiment. A theoretical plasma glucose step response 1052 is illustrated in diagram 1050 with an example resulting ISF glucose concentration 1054 superimposed for a unity gradient and first order time lag of 10 minutes. For such an example, it may take approximately 50 minutes or 5 time constants for the transient response from ISF glucose concentration to completely equilibrate.

As illustrated in FIG. 10(a), plasma glucose may be estimated from a measurement of ISF glucose through an electrochemical (e.g., current) sensor. A low current, which is usually in the nano Amp range, may be measured through an electrochemical reaction that is considered to be proportional to ISF glucose. These sensors and/or measurements there from may be subsequently calibrated via a BG sample measured with the use of a BG monitor.

Figure 11:
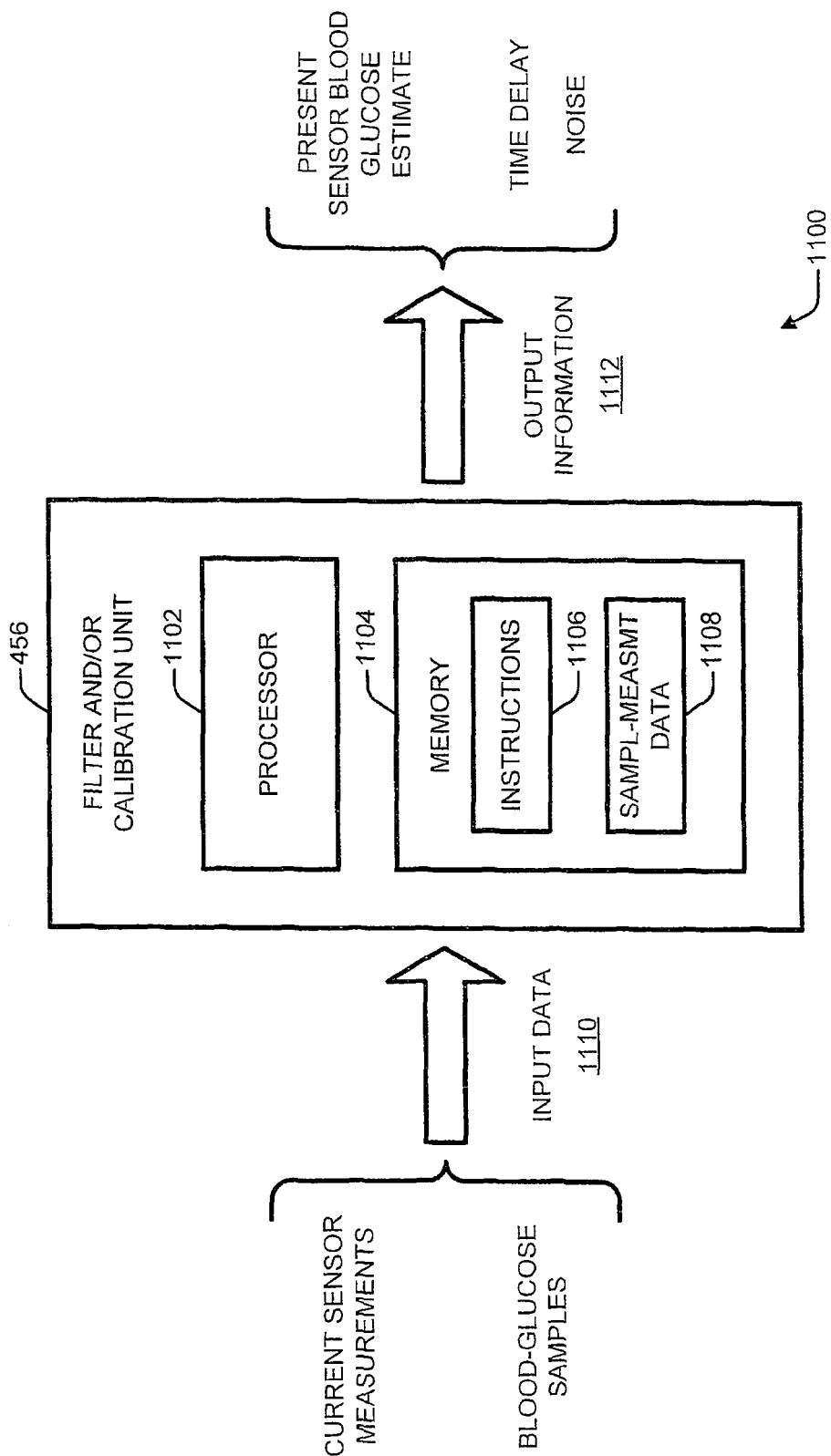
FIG. 11 is a block diagram of an example filter and/or calibration unit that produces output information based on, input data in accordance with an embodiment.

FIG. 11 is a block diagram 1100 of an example filter and/or calibration unit 456 that produces output information 1112 based on input data 1110 in accordance with an embodiment. As illustrated, filter and/or calibration unit 456 may include one or more processors 1102 and at least one memory 1104. In certain example embodiments, memory 1104 may store or otherwise include instructions 1106 and/or sample-measurement data 1108. Sample-measurement data 1108 may include, by way of example but not limitation, blood glucose reference samples measured via a blood sample, blood glucose sensor measurements, blood glucose sample-sensor measurement pairs, combinations thereof, and so forth.

In particular example implementations, filter and/or calibration unit 456 of FIG. 11 may correspond to filter and/or calibration unit 456 of FIG. 9. Input data 1110 may include sensor measurements (e.g., from an ISF current sensor), blood-glucose reference samples, and so forth, just to name a few examples. Output information 1112 may include a present blood-glucose concentration estimate based, at least in part, on sensor measurements; time delay(s); noise; and so forth, just to name a few examples.

Current sensor measurements of input data 1110 may correspond to sensor signal 16 (e.g., of FIGS. 1 and 9) and/or values resulting there from. Blood glucose reference samples may correspond to values acquired through, e.g., a finger stick test. They may be manually or automatically provided to filter and/or calibration unit 456. Output information 1112 may correspond to a present blood glucose concentration estimate G 452 (e.g., of FIG. 9) and/or values derived there from.

In certain example embodiments, input data 1110 may be provided to filter and/or calibration unit 456. Based on input data 1110, filter and/or calibration unit 456 may produce output information 1112. Current sensor measurements and/or blood glucose reference samples that are received as input data 1110 may be stored as sample-measurement data 1108.

Filter and/or calibration unit 456 may be programmed with instructions 1106 to perform algorithms, functions, methods, etc.; to implement attributes, features, etc.; and so forth that are described herein. Filter and/or calibration unit 456 may therefore be coupled to at least one blood glucose sensor to receive one or more signals based on blood glucose sensor measurements.

A filter and/or calibration unit 456 that comprises one or more processors 1102 may execute instructions 1106 to thereby render the unit a special purpose computing device to perform algorithms, functions, methods, etc.; to implement attributes, features, etc.; and so forth that are described herein. Processor(s) 1102 may be realized as microprocessors, digital signal processors (DSPs), application specific integrated circuits (ASICs), programmable logic devices (PLDs), controllers, micro-controllers, a combination thereof, and so forth, just to name a few examples. Alternatively, an article may comprise at least one storage medium (e.g., such as memory) having stored thereon instructions 1106 that are executable by one or more processors.

Figure 12:
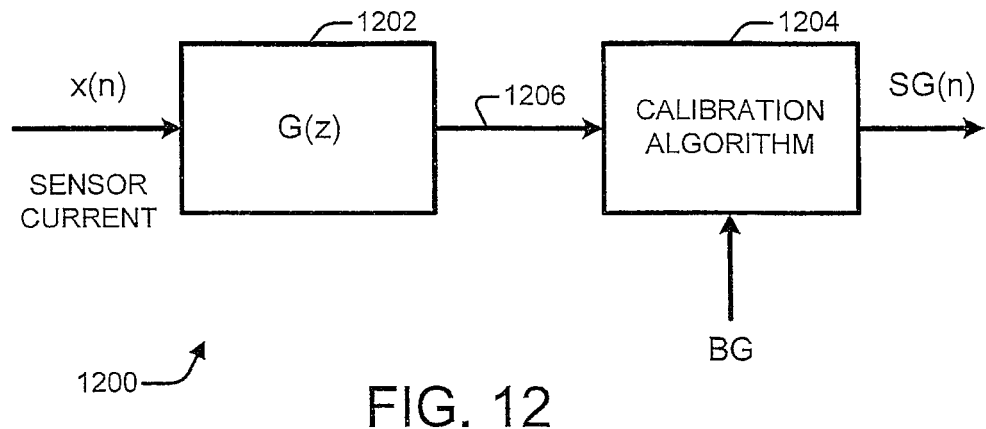
FIG. 12 is a block diagram of an example filter and calibration algorithm unit in accordance with an embodiment.

FIG. 12 is a block diagram of an example filter and calibration algorithm unit 1200 in accordance with an embodiment. As illustrated, filter and calibration algorithm unit 1200 may include a filter 1202 and a calibration algorithm 1204. For certain example embodiments, blocks 1202 and 1204 jointly show an example process for calibrating a raw sensor signal. A sensor current sample x(n) may be provided to filter 1202, which may produce an output signal 1206. Output signal 1206 and blood glucose reference samples (BG) may be provided to calibration algorithm 1204. Calibration algorithm 1204 may produce sensor glucose SG(n), which may correspond to blood glucose measurement values derived from sensor glucose measurements.

Filter 1202, as represented by G(z), may perform time lag correction and/or noise smoothing (e.g., using a Wiener and/or other filter). A filter residual output signal 1206 may be paired with BG samples, which may be acquired at approximately the same time, for calibration at calibration algorithm unit 1204. A resulting time-lag and noise-reduced signal may be calibrated by, e.g., linear regression at calibration algorithm unit 1204.

Figure 13:
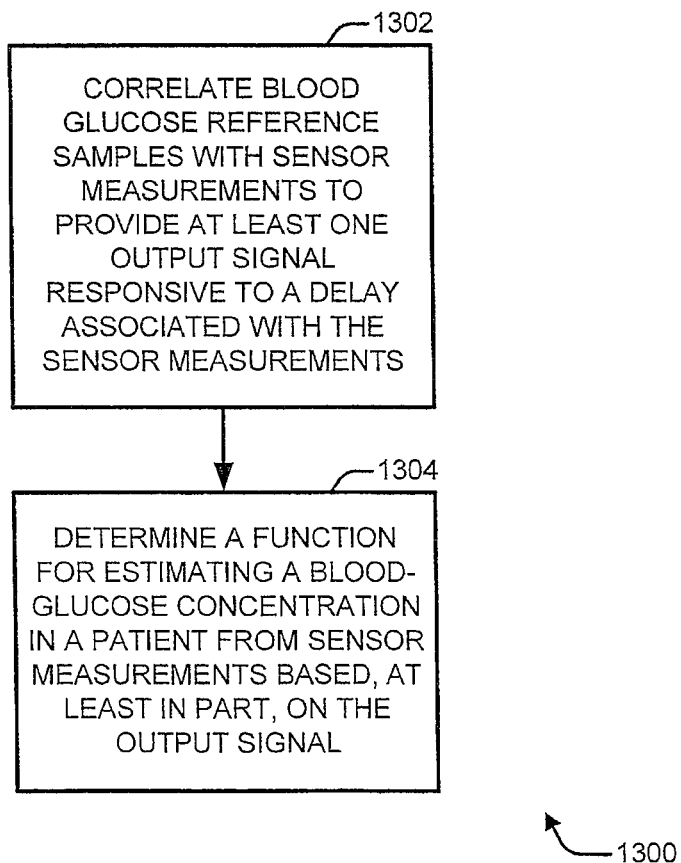
FIG. 13 is a flow diagram of an example method for calibrating a control system at least partly automatically in accordance with an embodiment.

FIG. 13 is a flow diagram 1300 of an example method for calibrating a control system at least partly automatically in accordance with an embodiment. As illustrated, flow diagram 1300 includes two operations 1302-1304. For certain example embodiments, at operation 1302, blood glucose reference samples may be correlated with sensor measurements to provide at least one output signal responsive to a delay associated with the sensor measurements. Such a correlation may be performed, for example, by a filter 1202. An example approach to determining a delay is described further herein below with particular reference to FIG. 15.

At operation 1304, a function for estimating a blood-glucose concentration in a patient from sensor measurements may be determined based, at least in part, on the at least one output signal. Such a function determination may be performed, for example, by calibration algorithm unit 1204. Although a certain number of operations are specifically illustrated in each flow diagram that is described herein, other embodiments may have a different number and/or different operations without departing from claimed subject matter.

Figure 14:
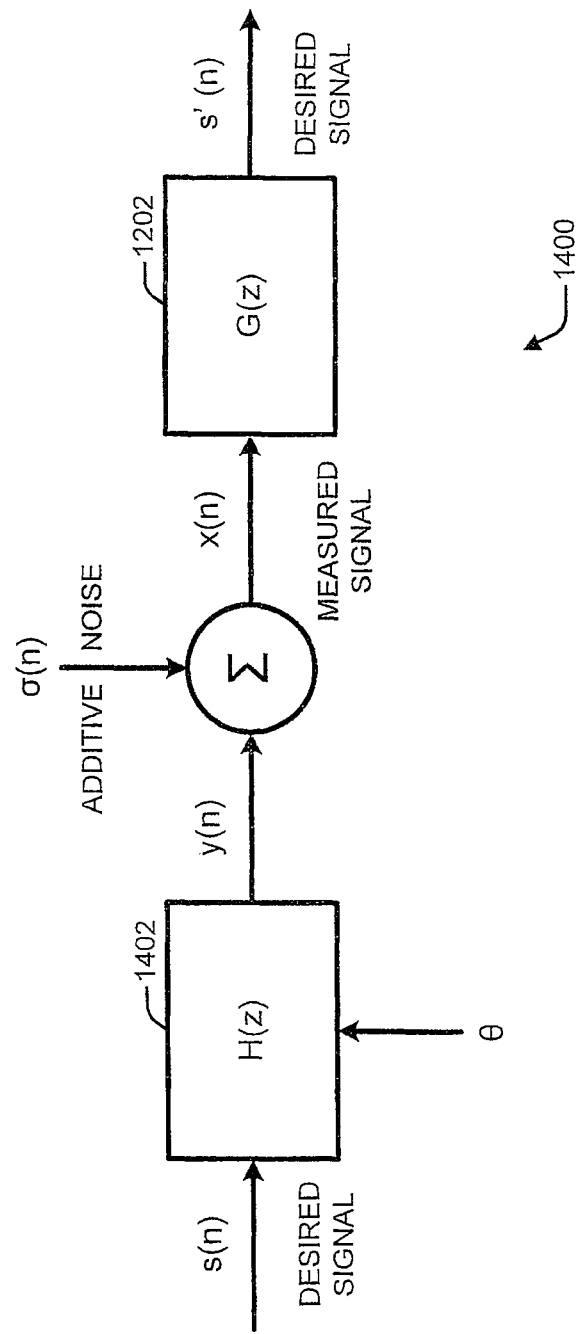
FIG. 14 is a block diagram that illustrates example phenomena, which may include a time delay and/or noise, that may affect a signal and a filter to at least partially account for such phenomena in accordance with an embodiment.

FIG. 14 is a block diagram of a model 1400 that illustrates (i) example phenomena, which may include a time delay and/or noise, that may affect a signal and (ii) a filter 1202 to at least partially account for such phenomena in accordance with an embodiment. As illustrated, example model 1400 includes a filter 1402 and a filter 1202, as well as a summer Z. Model 1400 illustrates example phenomena, such as a delay θ and/or noise a, that may distort or otherwise affect a desired signal s(n). Desired signal s(n) may represent blood glucose within a blood stream. When these phenomena impact a desired signal s(n), a measured signal x(n) may result.

For a model of certain example embodiments, a desired signal s(n) may be impacted by a delay θ, which effect may be modeled by filter H(z) 1402. This delay θ may represent a time lag introduced as glucose diffuses across a capillary boundary. Filter 1402 produces signal y(n). Noise, such as that caused by a sensor mechanism, is added to signal y(n) as a(n) to produce signal x(n), which may be a signal that is measured by a sensor. Filter G(z) 1202 attempts to account for delay θ and/or noise σ. By accommodating one or more of these phenomena, if a measured signal x(n) is input to filter 1202, a facsimile of desired signal s'(n) may be recreated.

In order to accommodate one or more of these phenomena, each phenomenon may be estimated. In order to approximate a delay between ISF glucose and plasma glucose, one or more correlations may be performed, for example. To perform one or more correlations, a matched filter, for example, may be employed. An example matched filter is shown in FIG. 15.

Figure 15:
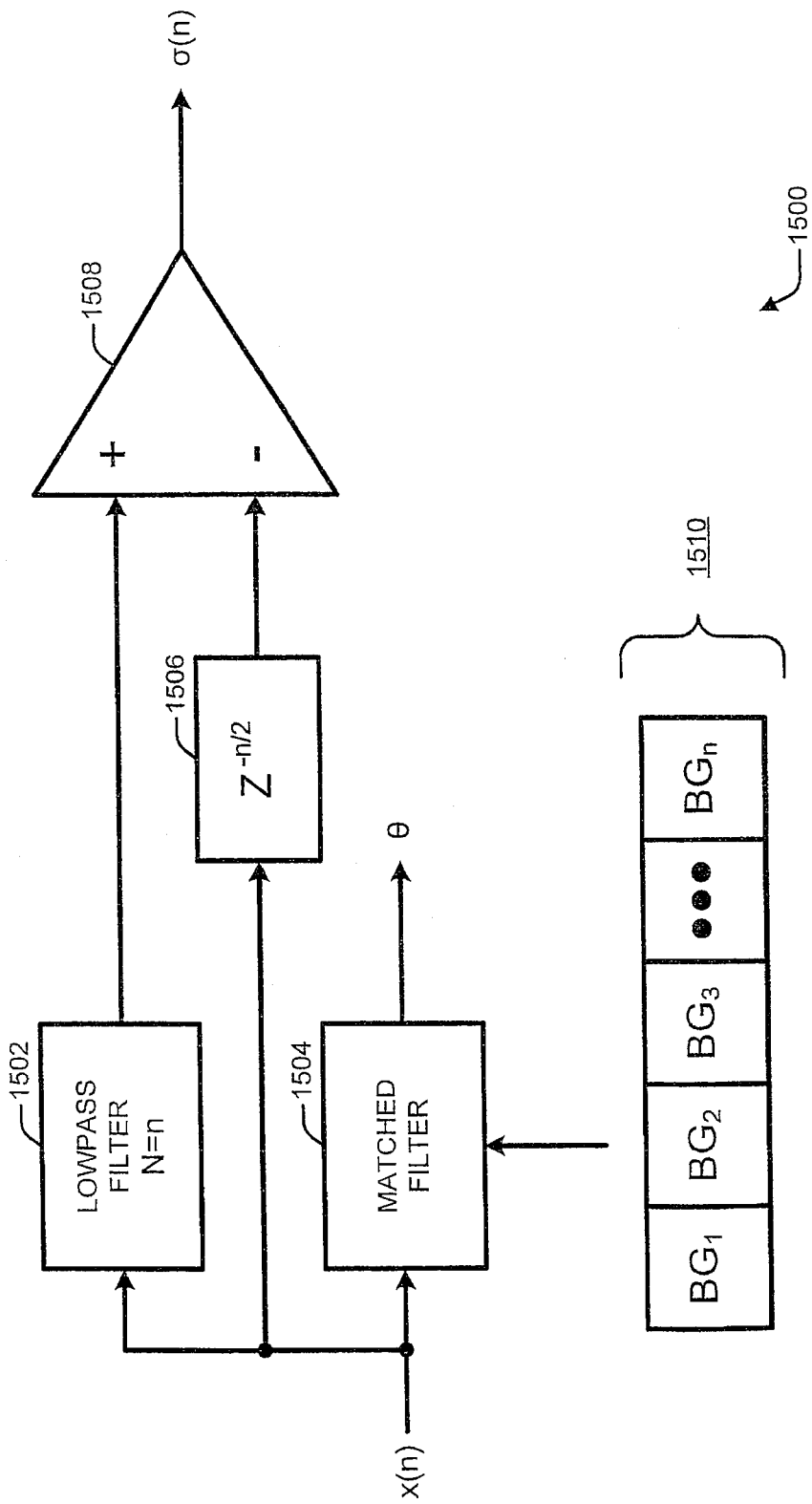
FIG. 15 is a block diagram that illustrates an example approach for determining a time delay and/or noise in accordance with an embodiment.

FIG. 15 is a block diagram 1500 that illustrates an example approach to determining a time delay θ and/or noise σ in accordance with an embodiment. As illustrated, block diagram 1500 may include a lowpass filter 1502, a matched filter 1504, a filter delay 1506, and a combiner 1508. Measured signal x(n) may be provided to lowpass filter 1502, matched filter 1504, and filter delay 1506. Combiner 1508 may receive output signals from lowpass filter 1502 and filter delay 1506 and produce noise σ(n).

In certain example embodiments, block diagram 1500 may also include multiple blood glucose samples 1510 ($BG_1$, $BG_2$, $BG_3$ ... $BG_n$). Matched filter 1504 may use a number of recent BG measurements for a BG sample template 1510 (e.g., n≥4). These BG sample measurements may be matched to a range of sensor measurements. By way of example, BG sample measurements may be paired with sensor measurements that are acquired at approximately the same time (e.g., during the same minute as the BG sample values) (e.g., t≈0). The sensor sequence of measurements may be time shifted by one sample (e.g., which may be one minute ahead in time), and sensor measurements may be paired with the template BG samples. This may be repeated for some number (e.g., 20) time shifts.

Each group of BG sample-sensor measurement pairs may be cross-correlated to measure a correlation for each time lag under analysis. The segment pair with the greatest correlation or highest magnitude output may be considered to represent a delay between current sensor and meter, or ISF and BG. This delay θ may be produced by matched filter 1504. A delay may be used to create a first order time lag for filter H(z) 1402, as shown in FIG. 14. An example matched filter may be represented by Equation (3):

$$y(i) = \sum_{k=0}^{N-1} BG(N-k-1) \cdot x(i-k) \quad (3)$$

where x(i) may be raw measurements of a sensor glucose signal, BG(k) may be samples of the template or BG measurement samples, N may be a filter length, and i may be a time shift index. If a BG template and sensor signal coincide or have a highest correlation, a matched filter output may be at a high value (e.g., a maximum) and that corresponding time index can be set to equal the time delay θ.

Sensor signal noise σ may be extracted by passing a sensor signal x(n) through a linear low-pass filter 1502 with enough stopband attenuation to remove much, if not most, of the noise. For a linear filter example, a filter-delay 1506 group delay may be half of its model order. Raw signal x(n) may be delayed by this degree as the filter order may be known at filter delay 1506, and the result thereof may be subtracted from a filtered signal output of lowpass filter 1502 at combiner 1508 to retain sensor noise σ.

This sensor noise signal may be passed to the model of FIG. 14 to develop filter coefficients (e.g., Wiener filter coefficients) for filter 1202. Coefficients for a time-lag correction filter (e.g., filter 1202) may be created based on diagram 1400 of FIG. 14 and/or using parameters (e.g., delay θ and/or noise a) determined through the approach or approaches illustrated in FIG. 15.

Distortion(s) in a signal channel may be ameliorated through channel equalization. A plasma-ISF channel equalization may be performed, for example, in accordance with the following. Signals that are transmitted through various types of mediums often undergo distortions in which a received signal is degraded or otherwise changed to some extent. The extent of degradation is governed, at least partially, by the intrinsic properties of a medium. One type of inverse filter that can be used to recover an original signal from a received signal is a Wiener filter. A Wiener filter provides a trade-off between inverse filtering and noise reduction. In case(s) of modeling a relationship between ISF glucose and plasma glucose, a medium may be considered to be a capillary wall that separates glucose measured within ISF space from that measured in plasma space.

A group of digital filter coefficients may be used to describe a diffusion process across a capillary wall. Block diagram 1400 of FIG. 14 outlines an example of such a procedure in which a signal to be obtained may be plasma glucose s(n). A signal that is acquired through an electrochemical biosensor and CGM device may be x(n)—a received or measurement signal. Measured signal x(n) may be distorted by one or more properties of a medium, e.g. a diffusion process as described above. In signal processing terms, a diffusion process may be equivalent to or otherwise analogized to convolving a plasma blood glucose signal s(n) with an impulse response h(n), which may represent a corrupting factor of a medium, to produce a degraded signal y(n):

$$y(n) = h(n) \otimes s(n) \quad (4)$$

This kind of dynamic relationship between plasma glucose and ISF glucose may be understood. An appropriate impulse response is therefore determinable and can be modeled by, e.g., an infinite-impulse-response (IIR) filter with a first-order lag. By way of example only, a first-order time lag may be τ=10 minutes with some gradient α. A time lag, however, may be calculated based on a time index delay determined via correlation (e.g., using a matched filter as described herein above with particular reference to FIG. 15). In the Laplace transform or S-domain, a model may be described using Equation (5):

$$H(s) = \frac{\alpha}{10s+1} \quad (5)$$

A transfer function in the z-domain may be expressed using Equation (6) below, where T is an example sample interval of one minute and α is a filter gain:

$$H(z) = \frac{z\alpha}{z - e^{-T/10}} = \frac{0.0952}{1 - 0.9048z^{-1}} \quad (6)$$

Filter gain α, which may be related to a (relatively constant) gradient between glucose concentration in ISF and plasma compartments, may be modified in the above equation to create a unity gradient, thereby providing a time lag between compartments and obviating a gradient term.

A received signal may be further degraded by additive white noise σ(n). It can also be further corrupted by a range of artifact(s) to produce a resultant acquired signal x(n):

$$x(n) = y(n) + \sigma(n) \quad (7)$$

In order to better estimate plasma glucose s(n), a set of optimal filter coefficients g(n) may be derived that can be used to filter a received ISF glucose signal and/or denoise additive interference. This may produce a usable estimate of plasma glucose as shown by Equation (8) as follows:

$$s'(n) = x(n) \otimes g(n) \quad (8)$$

Figure 16:
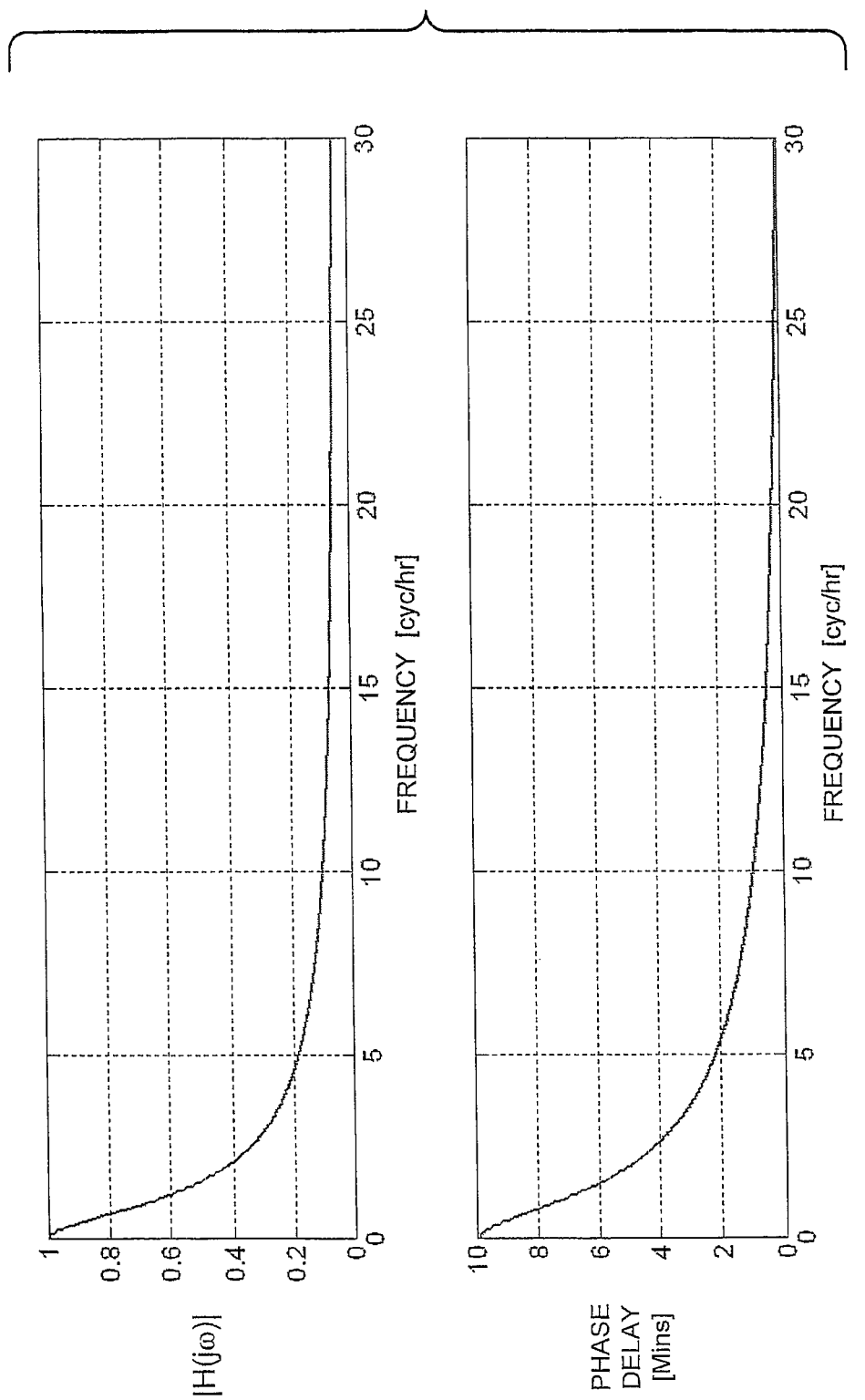
FIG. 16 depicts example graphical diagrams to illustrate frequency versus a phase delay and a delay-creating transfer function in accordance with an embodiment.
Figure 17:
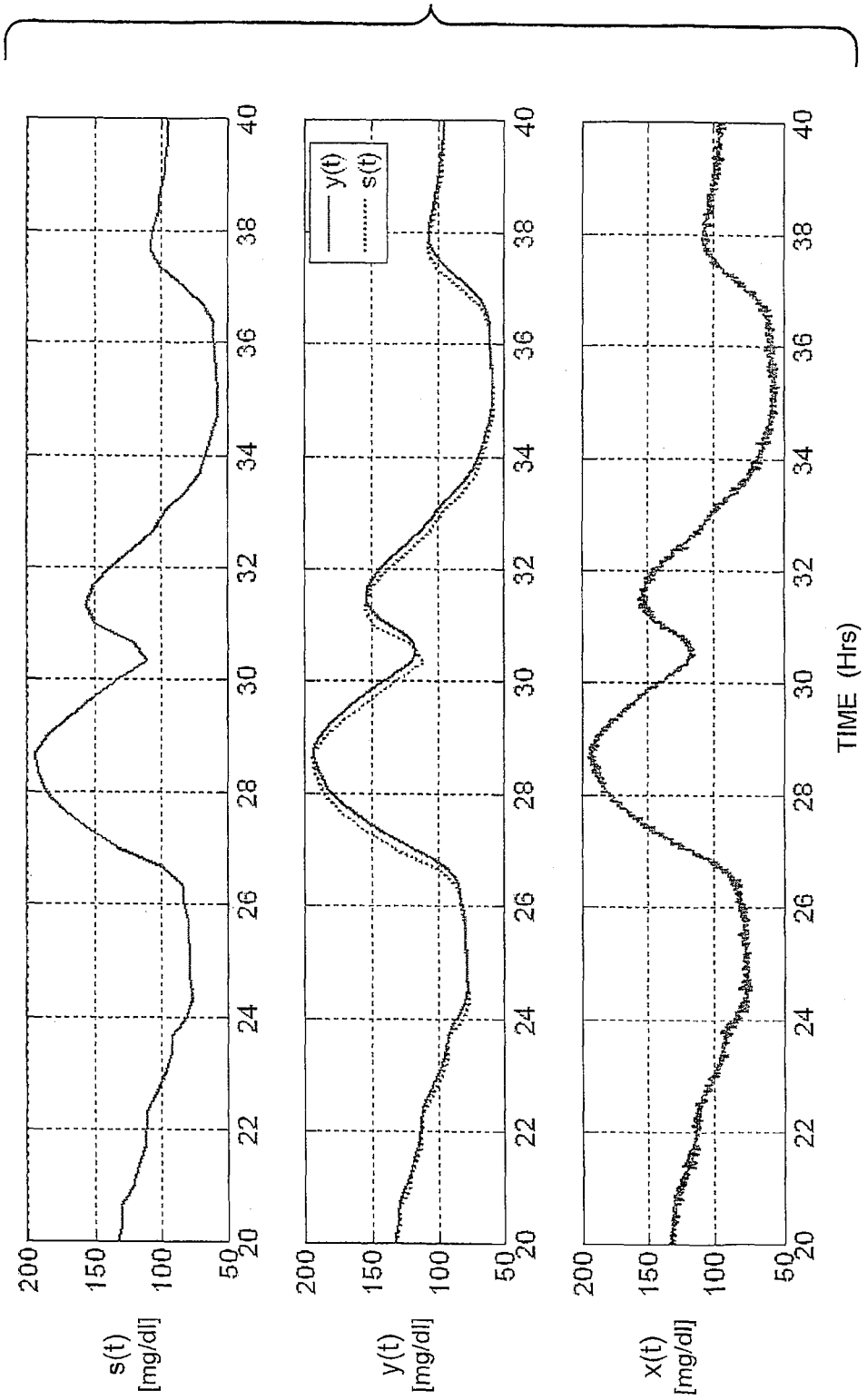
FIG. 17 depicts example graphical diagrams to illustrate time versus multiple signals in accordance with an embodiment.
Figure 18:
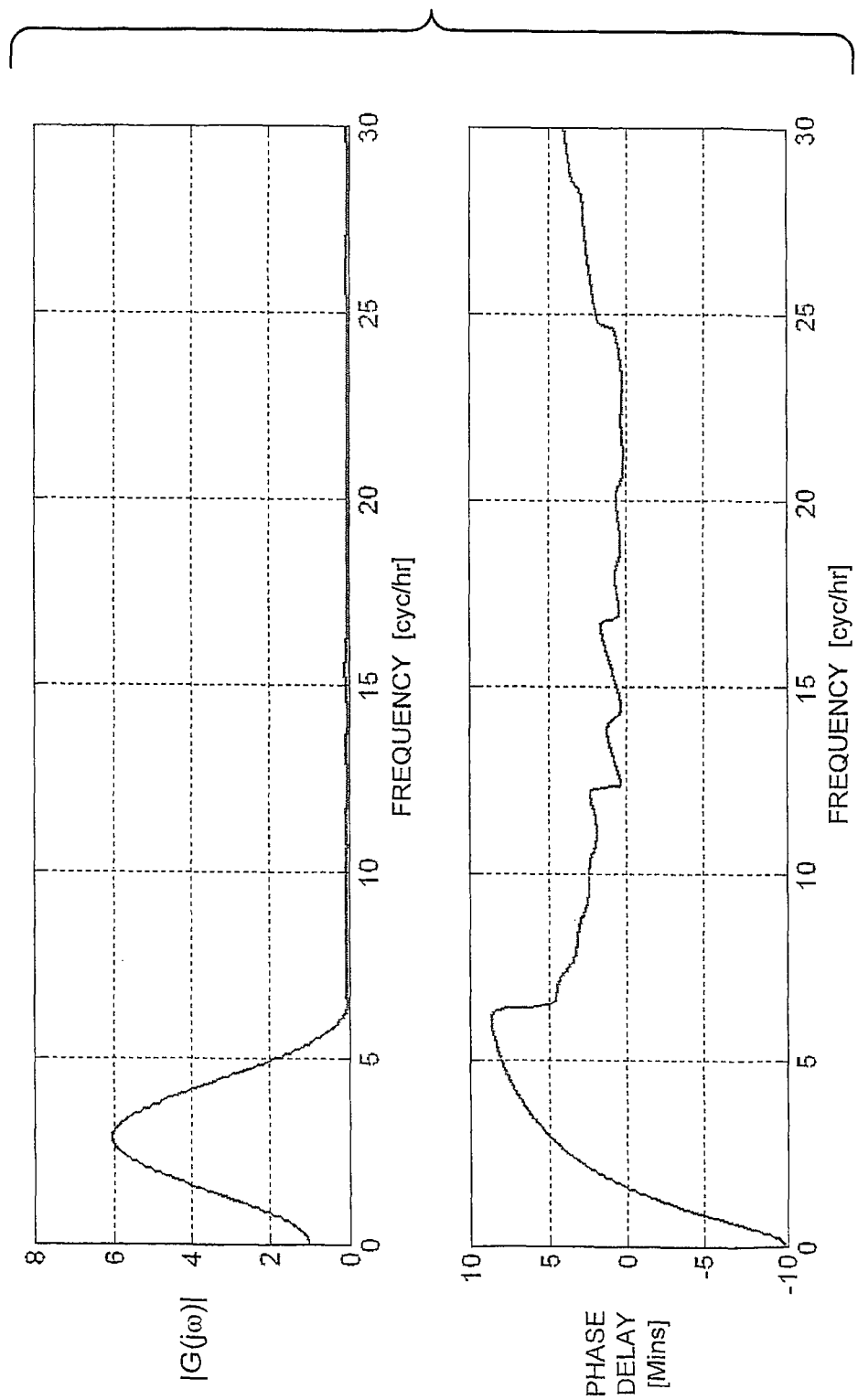
FIG. 18 depicts example graphical diagrams to illustrate frequency versus a phase delay and a corrective transfer function in accordance with an embodiment.

FIGS. 16-18 depict graphical diagrams to illustrate example conceptual implementations in accordance with certain embodiments. More specifically, FIG. 16 depicts example graphical diagrams 1600 to illustrate frequency versus a phase delay and a delay-creating transfer function in accordance with an embodiment. FIG. 17 depicts example graphical diagrams 1700 to illustrate time versus multiple signals in accordance with an embodiment. FIG. 18 depicts example graphical diagrams 1800 to illustrate frequency versus a phase delay and a corrective transfer function in accordance with an embodiment.

Example frequency and phase responses of filter H(z) (e.g., of FIG. 14) are illustrated in FIG. 16. An example 10 minute time delay can be identified at DC or 0 Hz. Glucose changes at a relatively very slow rate, at least in signal processing terms inasmuch as a signal of this type may be considered to be in the ultra-low frequency (ULF) range. Steady-state glucose may be measured at DC, and fast glucose digressions are typically observed at under 2-3 cycles per hour. In order to produce a group of filter coefficients to correct for ISF time lag, an electrochemical biosensor signal of 40 hours duration was modified to create "ideal" and measurement signals in this example. A reference signal was sampled every minute and decimated to create an "ideal" plasma glucose signal with a sample time interval of 20 minutes.

This "ideal" signal s(n) is illustrated by a first trace at the top of FIG. 17. An original biosensor signal with a one minute measurement time interval was processed by a diffusion filter H(z) with a first order time lag of 10 minutes to produce a time delayed signal y(n), which is illustrated by a second trace in the middle of FIG. 17. To model a sensor glucose signal acquired subcutaneously from ISF, Gaussian white noise may be added to a glucose signal to create a measurement signal x(n) with a signal-to-noise ratio (SNR) of 10 dB, which is shown by a third trace at the bottom of FIG. 17. Signals s(n) and x(n) may thus be used to create a group (e.g., a set) of filter coefficients (e.g., Wiener filter coefficients). Although white noise is used in this simulation example and reflected in the graphical diagrams, actual (estimated) sensor noise may be extracted and used as previously described herein above with particular reference to FIG. 15.

Although other type(s) of filters may alternatively be used without deviating from claimed subject matter, an example implementation that is described below employs a Wiener filter. More specifically, a Wiener filter implementation is described in the time-domain. For a so-called "optimal" FIR Wiener filter, the MSE may be the sum of the squares of the residuals given as:

$$\varepsilon = \sum_{k=0}^{N-1} |e(n)^2| = \sum_{k=0}^{N-1} |s(n) - s'(n)|^2, \quad (9)$$

which is equivalent to finding solutions to a number of Wiener-Hopf equations, as provided in Equation (10):

$$\sum_{n=0}^{p-1} g(n) r_{xx}(k-n) = r_{xy}(k), \quad k = 0, 1, \ldots p-1. \quad (10)$$

In matrix form, Equation (10) may be written instead as shown in Equation (11):

$$g_{opt} = R_{xx}^{-1} r_{xy}, \quad (11)$$

where $R_{xx}$ may be a Toeplitz matrix of an autocorrelation sequence $r_{xx}$ for a given dataset x:

$$r_{xx} = \sum_{k=0}^{N-1} x(k) x^*(k-n), \quad (12)$$

and $r_{xy}$ may be a cross-correlation sequence as shown in Equation (13):

$$r_{xy} = \sum_{k=0}^{N-1} s(k) x^*(k-n). \quad (13)$$

A desired signal may be estimated for p observations of a current sample:

$$s'(n) = \sum_{k=0}^{p-1} g(k) x(n-k) = g^h x(n), \quad (14)$$

$$g = [g_0, g_1, \ldots, n-p+1]^T.$$

For real values, an autocorrelation matrix may be symmetrical. In the above derivation, it is assumed, without loss of generality or limitation, that autocorrelation and cross-correlation sequences are known. In a case of correcting for ISF time lag, such sequences may be estimated from data samples. An approach that may be adopted to derive time domain Wiener filter coefficients is described by Equation (15):

$$g_{opt} = (Y^T Y)^{-1} Y^T s \quad (15)$$

In the above Equation (15), Y may be a Toeplitz matrix of data samples x (e.g., measurement signal) in which a resultant matrix multiplication inside the parenthesis may be a time-averaged autocorrelation estimate of an input signal. Its inverse may be multiplied by a time-averaged cross-correlation estimate of both input and desired signals (e.g., terms outside parenthesis).

This approach may use a complete data block formulation to derive a group of coefficients. It can be shown to approach a Wiener filter of Equation (11) as the data block length approaches ∞. A time domain Wiener filter may be created for this example by applying measurement (x(n)) and desired (s(n)) signals of FIGS. 14 and 17 to Equation (15). A frequency response of a Wiener filter (G(z)) is illustrated in an upper graph of FIG. 18 where filter smoothing properties are apparent with a high degree of noise suppression above about 6 cycles/hour. Phase correction properties may be seen from a phase response illustrated in a lower trace of FIG. 18. A phase correction of 10 minutes is apparent at DC in the lower graph.

For certain example embodiments, methods of calibration for glucose sensor current (Isig) to reflect blood glucose reference sample (BG) values are described. Three example parameters may be estimated. These three example parameters may include a calibration factor (CF), a current offset (○), and a delay (Δ) between subcutaneous glucose and blood glucose. Calibration method(s) may produce results without explicit consideration of a variable delay if a manual BG reference sample measurement is taken during an interval of relatively, if not nearly, constant glucose levels. However, it may enhance calibration accuracy if calibration is performed on rapidly changing glucose levels. Because glucose variability can often be encountered without a specific cause in subjects with diabetes, certain implementations of this method may help to ease fasting requirements prior to measurement. Certain implementations may also be used in emergency situations when re-calibration is desired in spite of a possible ongoing glucose excursion.

A relationship formula that may include both BG and Isig is considered next: BG(t)=CF×(Isig(t+Δ)−○), where Isig(t+Δ) may be sensor current measured at time "t" plus shift "delta" (Δ). Given that BG may be changing relatively slowly, "D" may be selected to be a time interval for which it is acceptable to assume, without loss of generality or limitation, that change is relatively gradual. During such a time interval D, a smoothed Isig may be approximated as a linear function: Isig=A*t+B, where t is changing from 0 to D. Time interval D may be chosen from, e.g., 5 to 15 minutes, and sensor current may be measured, e.g., every minute. However, other time periods, sampling intervals, frequencies, etc. may alternatively be selected without departing from claimed subject matter.

The equation for BG that is presented above may be solved by substituting a linear relationship and finding BG estimates for instances of time from t to t+D. Reverting back to the original equations where CF and ○ are unknowns and Δ is fixed, it may be solved. An equation for BG may be solved, for example, in a least-squares sense using singular value decomposition (e.g., a number of equations is D, and a number of unknowns is two). Repeating this procedure for different delays Δ can provide a series of solutions with their corresponding errors. A solution with a lowest or minimal error (e.g., from a given series of solutions) may be chosen in order to estimate a delay Δ.

Certain implementations of this method may be used with a single or with multiple BG sample measurements by combining series of equations from different instances of BG observations. Certain implementations of this method may be relatively simple and computationally efficient because a dimension of matrices may be at most D×D for a single point calibration.

Sensor data may be calibrated while a glucose and/or insulin system is functioning (e.g., online calibration of sensor current may be performed). In certain example embodiments, a continuous glucose monitoring sensor (CGMS) may output a current signal (isig, nAmps), which may be considered to linearly correlate with blood glucose concentration (BG, mg/dL). Hence, a linear calibration model may be used to calculate a sensor glucose concentration (SG, mg/dL) from isig, as shown below in Equations (16) and (17):

$$SG(t) = CF \times isig(t) - CFOS \quad (16)$$

$$CFOS = CF \times OS \quad (17)$$

Here, CF (calfactor) and OS (offset) are two parameters (P) of an example model that is capable of capturing a linear relationship between a sensor current signal and blood glucose concentration.

In order to estimate parameters for the above example model, blood glucose concentration may be sampled periodically with the help of a, e.g., finger-stick BG-meter. An accurate estimation of parameters may be challenging if sensor characteristics change significantly with time. Moreover, infrequent reference blood glucose measurement samples may make parameter estimation even more difficult. On the other hand, finding appropriate calfactor and offset values may improve sensor performance, especially during hyperglycemic and hypoglycemic periods. The following description contains three different example techniques that may be used to estimate parameters of Equations (16) and (17). Example methods to evaluate a performance of each technique are also described below. Although three parameter estimation techniques that utilize at least one probability model are described herein below, claimed subject matter is not so limited, and other parameter estimation techniques may alternatively be implemented.

Figure 19:
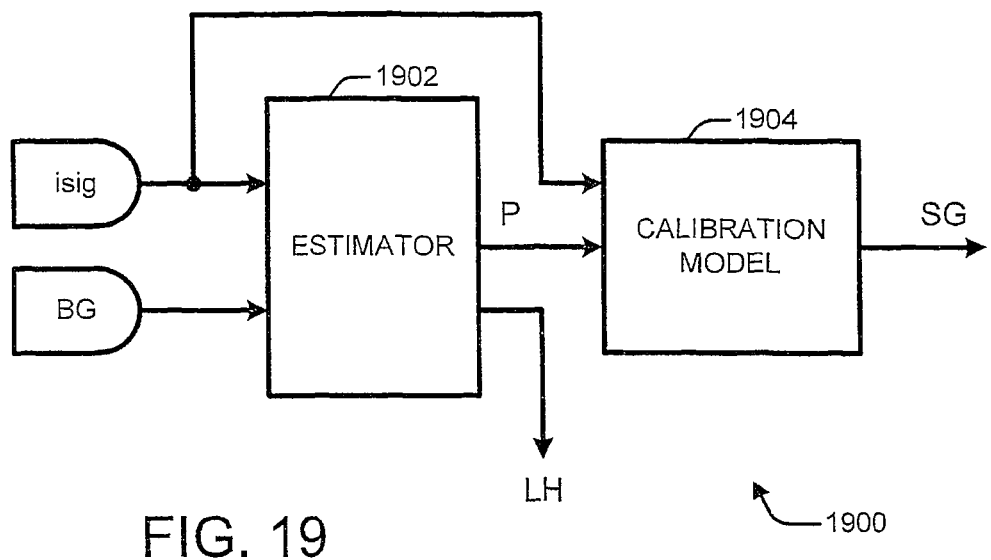
FIG. 19 is a block diagram that illustrates an example estimator and calibration model unit to determine sensor glucose in accordance with an embodiment.

FIG. 19 is a block diagram 1900 that illustrates an example estimator 1902 and calibration model unit 1904 to determine sensor glucose (SG) in accordance with an embodiment. As illustrated, block diagram 1900 may include sensor current (isig) and reference blood glucose concentration (BG) input signals to estimator 1902. Estimator 1902 may provide estimated parameters (P) and a likelihood (LH) value. Calibration model unit 1904 may produce sensor glucose SG from sensor current isig and parameters P.

For certain example embodiments, block diagram 1900 illustrates an example parameter estimation for a sensor calibration model. Estimator 1902 may represent any type of estimation approach whose function is to estimate parameters of Equation (16), including one or more probability models. Example estimation approaches include, but are not limited to, a Kalman filter (KF), a Kalman filter with adaptive process noise matrix (KFQ), an unscented Kalman filter, a Bayesian inference algorithm (B), some combination thereof, and so forth.

Input data to estimator 1902 may comprise sensor current (isig) and reference blood glucose concentration (BG). Output data of estimator 1902 may comprise an estimated parameter vector, P (e.g., P=[CF; OS] for Equation (16)), and a likelihood value, LH. A likelihood value LH, or more generally a quality indicator, may indicate a performance level of a calibration model. A parameter vector, P, along with sensor current, isig, may be fed to a calibration model unit 1904 in order to calculate sensor glucose concentration (SG). Although one estimator 1902 and one calibration model unit 1904 are shown in block diagram 1900, more than one of either or both may be implemented. For example, two estimators, E1 and E2, may be used in parallel, as is described herein below with particular reference to FIG. 21. Although a likelihood value is described as an example quality indicator to indicate a performance accuracy of a calibration model, claimed subject matter is not so limited, and other quality indicators may alternatively be implemented.

Figure 20:
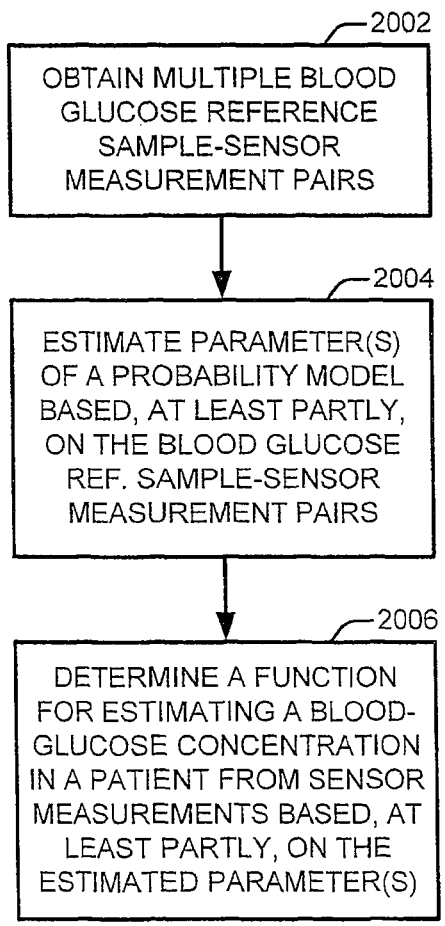
FIG. 20 is a flow diagram of an example method for online calibration of sensor measurements using one or more probability models in accordance with an embodiment.

FIG. 20 is a flow diagram 2000 of an example method for online calibration of sensor measurements using one or more probability models in accordance with an embodiment. As illustrated, flow diagram 2000 includes three operations 2002-2006. For certain example embodiments, at operation 2002, multiple blood glucose reference sample-sensor measurement pairs may be obtained. At operation 2004, one or more parameters of a probability model may be estimated based, at least in part, on the multiple blood glucose reference sample-sensor measurement pairs. Such an estimation of parameter(s) may be performed, for example, by estimator 1902.

At operation 2006, a function for estimating a blood-glucose concentration in a patient from sensor measurements may be determined based, at least in part, on the estimated one or more parameters. Such a determination of a function may be performed, for example, by calibration model unit 1904. Although a certain number of operations are specifically illustrated in each flow diagram that is described herein, other embodiments may have a different number and/or different operations without departing from claimed subject matter.

Three example probability models are described below that may be used to estimate parameters P by an estimator 1902. However, embodiments may implement alternative probability model(s) without departing from claimed subject matter. Example Linear Kalman Filter (KF): A linear Kalman Filter (KF) may have two stages: a prediction stage, in which a current stage of a system is predicted given a previous stage; and an update stage, in which a current predicted stage of the system is updated/corrected based on a weighted error generated between a model prediction and a true measurement. Certain example implementations for prediction stages and update stages may be realized using the following Equations (18)-(24):

Prediction $$x_k^- = A_{k-1} x_{k-1} \quad (18)$$

$$P_k^- = A_{k-1} P_{k-1}^- A_{k-1}^T + Q_{k-1} \quad (19)$$

Update:

$$v_k = y_k - H_K x_k^- \quad (20)$$

$$S_k = H_k P_k^- H_k^T + R_k \quad (21)$$

$$K_k = \frac{P_k^- H_k^T}{S_k} \quad (22)$$

$$x_k = x_k^- + K_k v_k \quad (23)$$

$$P_k = P_k^- - K_k S_k K_k^T \quad (24)$$

Here, $x_k^-$ and $P_k^-$ may be a predicted mean and a covariance of the state, respectively, on a time stage k prior to a measurement. In this case, $x_k^- = [CF^-; CFOS^-]$. Variables $x_k$ and $P_k$ may comprise a corrected mean and a covariance of a state, respectively, on a time stage k after seeing a measurement. Variable $v_k$ may be a measurement residual on time stage k. $S_k$ may be a measurement prediction covariance, and $K_k$ may be a filter gain on time stage k. $A_{k-1}$ may represent a transition matrix of a dynamic model for a time stage k−1, and $H_k$ may be a measurement model matrix for a time stage k. In this case, $H_k = [\text{isig}(k), -1]$. The superscript '−' sign indicates that such variables correspond to prior to an update at a given time stage.

$Q_{k-1}$ may be a process noise on time stage k−1, and $R_k$ may be measurement noise on time stage k. Both of these noise matrices may be maintained constant throughout the length of an operation. Also, $y_k$ may be an available measurement on a time stage k. A parameter vector, $x_k$ (where $x_k = [CF; CFOS]$), may be updated whenever blood glucose measurement ($y_k = BG(k)$) is available.

Example Linear Kalman Filter With Adaptive Process Noise Matrix (Q): A linear Kalman filter with an adaptive Q-matrix (KFQ) has similar operating stages as those described above with regard to a Kalman filter (KF). A difference is that a process noise matrix, $Q_k$, may be a function of model performance. If BG is available, $Q_k$ may be updated as shown below in Equation (25)

$$Q_k = K_k (y_k - H_k x_k^-)^2 K_k. \quad (25)$$

A larger residual may result in a larger Q-matrix, which may in turn lead to a smaller $K_k$ per stage. In other words, if a model were not performing well due to a large process noise, a resulting Kalman gain ($K_k$) may be less aggressive. Such an adaptive feature may be relevant to a system where sensor related artifacts and/or noises are relatively common. Potentially, an example KFQ implementation may reduce the chances of capturing noise in estimated parameters.

Example Linear Kalman Filter With Adaptive Measurement Noise Matrix (R): A linear Kalman filter with an adaptive R-matrix (KFR) has similar operating stages as those described above with regard to a Kalman filter (KF). A difference is that a measurement noise matrix, $R_k$, may be a function of model performance. If BG is available, $R_k$ may be updated as shown below in Equation (26)

$$R_k = (y_k - H_k x_k^-)^2 \quad (26)$$

A larger residual may result in a larger R-matrix, which may in turn lead to a smaller $K_k$ per stage. In other words, if a model were not performing well due to a large measurement noise, a resulting Kalman gain ($K_k$) may be less aggressive. Hence, an implementation of KFR may reduce the chances of capturing noise in estimated parameters. As noted above, a linear Kalman filter may also be implemented with regard to both process noise and measurement noise. For example, a KF may be implemented in which both an adaptive Q-matrix and an adaptive R-matrix are updated based on a residual.

Example Bayesian Inference Approach (B): A general representation of a sensor glucose calibration model in terms of an example Bayesian inference approach can be written as follows:

$$y = f(X, \theta). \quad (27)$$

Here, X may be an independent variable (isig), and θ may be a parameter vector (θ = [CF; OS]). A dependent variable (SG) may be represented by y. A Bayesian approach (B) may represent uncertainty about unknown parameter values by probability distributions, and it may proceed as if parameters were random quantities.

A posterior parameter distribution may be given by Baye's theorem as follows:

$$\pi(\theta \mid Y) = \frac{\pi(\theta)\pi(Y \mid \theta)}{\int \pi(\theta)\pi(Y \mid \theta)d\theta}, \quad (28)$$

where Y may be a vector of measurements, $\pi(\theta)$ may be a prior parameter distribution, $\pi(\theta|Y)$ may be a posterior parameter distribution, and $\pi(Y|\theta)$ may be a likelihood function. The likelihood, for certain example implementations, may be a probability of data Y given parameters θ. Likelihood values may be determined from a probability distribution of errors between modeled and observed data. However, analytical integration of the denominator in Equation (27) has been a source of some difficulty in applications of Bayesian inference. Monte Carlo integration using Markov Chain Monte Carlo (MCMC) is one approach to addressing this difficulty.

A Metropolis-Hastings algorithm: A Metropolis-Hastings (MH) algorithm is an example MCMC technique for generating samples from a posterior distribution $\pi(\theta|Y)$. An MH algorithm may start with a vector value $\theta_0$. For example implementations, a sequence of N parameter vectors $\theta_i$, i=1, ..., N, may be generated as follows:

1. Generate a candidate parameter vector θ* from a proposal distribution for instance a normal distribution with mean equal to $\theta_{i-1}$.
2. Calculate T in accordance with Equation (29) below:

$$T = \frac{\pi(Y \mid \theta^*)\pi(\theta^*)q(\theta_{i-1} \mid \theta^*)}{\pi(Y \mid \theta_{i-1})\pi(\theta_{i-1})q(\theta^* \mid \theta^{i-1})} \quad (29)$$

where $\pi(Y|\theta^*)$ and $\pi(Y|\theta_{i-1})$ may be maximum likelihood values of parameter vectors θ* and $\theta_{i-1}$, respectively, and $\pi(\theta^*)$ and $\pi(\theta_{i-1})$ may be prior densities of θ* and $\theta_{i-1}$, respectively.

3. If min(1,T)>u, where u is drawn from a uniform distribution on the interval (0,1), then $\theta_i=\theta^*$, else $\theta_i=\theta_{i-1}$.

After an initial phase of say M iterations, a chain thus constructed may likely converge to a chain with elements randomly drawn from a posterior parameter distribution $\pi(\theta|Y)$. A first M iterations may be discarded. A sample of parameter vectors $\theta_i$, i=M+1, ..., N, may be used to calculate a posterior means as follows using Equation (30):

$$\bar{\theta} = \frac{1}{N-M}\sum_{i=M+1}^{N}\theta_i \quad (30)$$

Vector $\bar{\theta}$ may be considered as an estimate of model parameters. A sample of parameter vectors may also be used for calculating posterior variances, correlations between parameters, and distribution of model prediction.

Example calculation of maximum likelihood function: The following example function of Equation (31) may be used to calculate a maximum likelihood:

$$\pi(Y \mid \theta) = \prod_{j=1}^{K}(2\pi\sigma_j^2)^{-1/2}\exp\left\{\frac{-[y_j - f(x_j;\theta)]^2}{2\sigma_j^2}\right\} \quad (31)$$

where $y_j$ may be a jth y value in a dataset Y, $x_j$ may be a vector of explanatory (e.g., independent) variables associated with $y_j$, $f(x_j,\theta)$ may be a model prediction of $y_j$, $\sigma_j$ may be a standard deviation associated with the jth value in a data set, and K may be a total number of data in a data set.

Generally, parameter estimation by a Bayesian approach is relatively more robust when both process and measurement noises are present. However, a drawback of such a method is that Bayesian approaches can be relatively computationally intensive.

An example technique for evaluating estimator performance is described. For certain example embodiments, a performance of each estimator (e.g., estimator 1902) may be evaluated based on a bias (e.g., error) between model estimates and "true" values. Many different functions may be used to evaluate estimator performance. If model errors are assumed to be independent and normally distributed, the following likelihood function, by way of example but not limitation, may be used:

$$LH = \frac{1}{\sigma_j\sqrt{2\pi}}\exp\left\{\frac{-[y_j - \bar{y}_j]^2}{2\sigma_j^2}\right\} \quad (32)$$

Here, $y_j$ may be a "true" value (e.g., data) at a jth stage, and $\bar{y}_j$ may be a model prediction at a jth stage (where, $\bar{y}_j$=CF×isig$_j$–CFOS). $\sigma_j$ may represent a standard deviation of a model estimate at a jth stage due to variation in CF and CFOS parameter values.

Generally, a larger model error may result in a drop in an LH value. During a calibration phase, after detecting a measurement if an estimated LH value is less than a prior LH value by a certain predetermined margin, an extra confirmation finger-stick measurement may be requested. Although a particular example (e.g., LH-based) function has been used to evaluate performance of estimator(s), claimed subject matter is not so limited, and other (e.g., error-characterizing) evaluation functions may alternatively be implemented.

Figure 21:
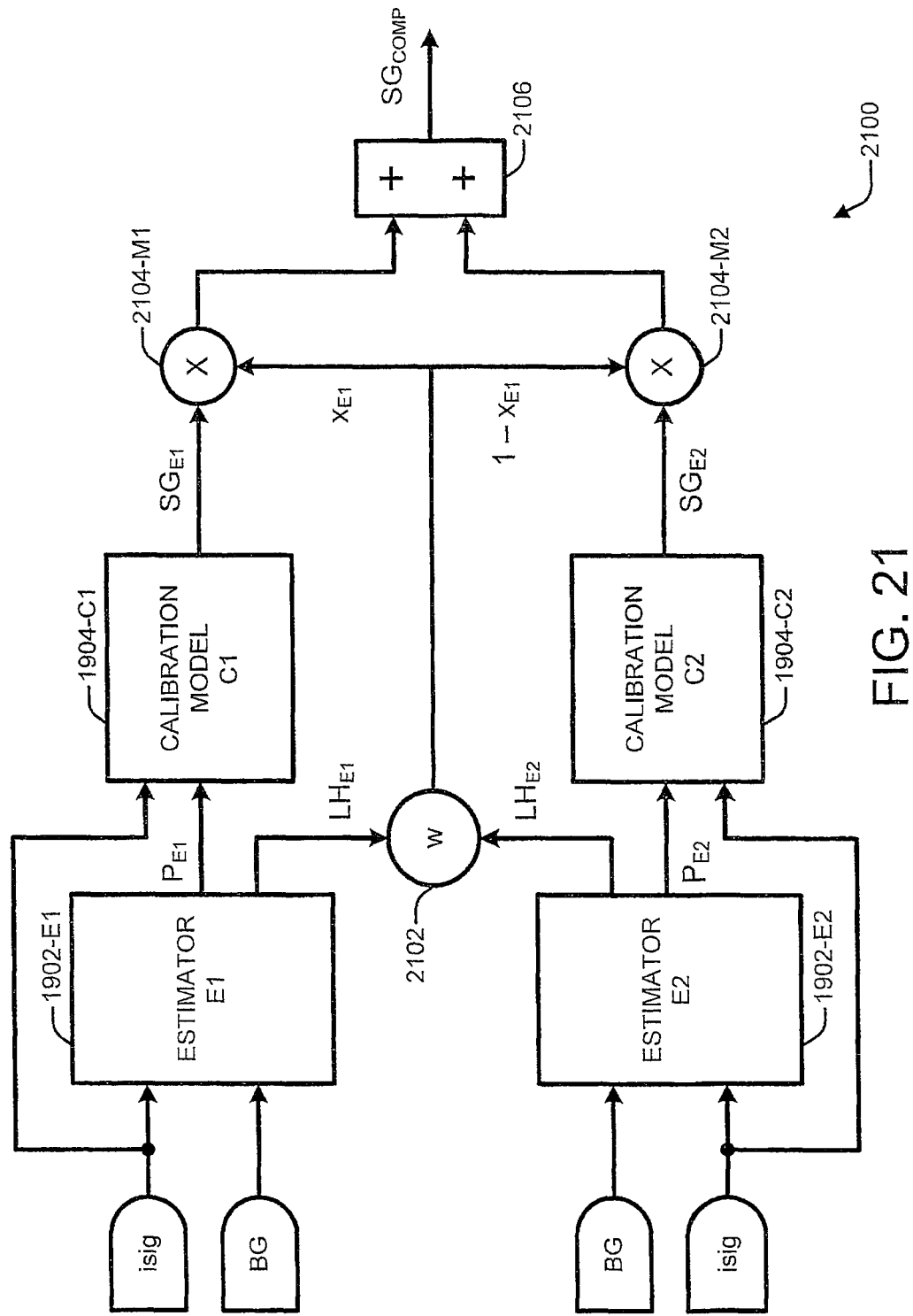
FIG. 21 is a block diagram that illustrates multiple example estimators and calibration model units to determine a composite sensor glucose in accordance with an embodiment.

FIG. 21 is a block diagram 2100 that illustrates multiple example estimators 1902 and calibration model units 1904 to determine a composite sensor glucose ($SG_{COMP}$) in accordance with an embodiment. As illustrated, block diagram 2100 may include two estimators 1902-E1 and 1902-E2, two calibration model units 1904-C1 and 1904-C2, a weighting unit 2102, and two mixers 2104-M1 and 2104-M2. It may also include a combining unit 2106.

For certain example embodiments, two estimators, E1 and E2, may be used in parallel. Based on performances of an E1-estimator ($LH_{E1}$) and an E2-estimator ($LH_{E2}$), respective weights at weighting unit 2102 may be assigned ($x_{E1}$ and $1-x_{E1}$) to respective sensor glucose concentrations ($SG_{E1}$ and $SG_{E2}$). These respective sensor glucose concentrations ($SG_{E1}$ and $SG_{E2}$) may be provided by respective calibration models, C1 and C2. Respective weights and sensor glucose concentrations (as indicated by E1 and/or E2 in block diagram 2100) may be provided to mixers M1 and M2. Output signals from mixers M1 and M2 may be used to calculate a composite sensor glucose concentration ($SG_{comp}$) with combining unit 2106.

As shown in FIG. 21, more than one estimator may be used in parallel to calculate a sensor glucose concentration (SG). For example, two estimators E1 and E2 may be implemented. In such cases, a Kalman filter (KF) and a Bayesian inference estimator (B), for instance, may be used to estimate parameters of an, e.g., linear model, relatively or effectively simultaneously. A contribution of each estimator may be computed by comparing their performances in terms of a, e.g., likelihood function at a weighting unit 2102.

Such a comparison may be achieved, for example, by using the following Equation (33):

$$x_{E1} = \frac{LH_{E1}}{LH_{E1} + LH_{E2}} \quad (33)$$

Here, $LH_{E1}$ and $LH_{E2}$ may be likelihood values of E1- and E2-estimators (e.g., KF- and B-estimators), respectively. $x_{E1}$ may be a fractional weight of an E1-estimator.

Conversely, $1-x_{E1}$ may be a fractional weight of an E2-estimator. A composite sensor glucose ($SG_{comp}$) value from both of these two or more estimators may be calculated as follows using example Equation (34) with mixers 2104-M1 and 2104-M2 plus combiner 2106:

$$SG_{comp}=SG_{E1} \times x_{E1} SG_{E2} \times (1-x_{E1}) \quad (34)$$

Here, $SG_{E1}$ and $SG_{E2}$ may be sensor glucose concentrations calculated by E1- and E2-estimators, respectively. Although FIG. 21 includes two estimators, claimed subject matter is not so limited, and results from three or more estimators may also be combined into a composite sensor glucose value. Also, although an example above describes using one KF estimator and one B estimator, claimed subject matter is not so limited. Alternative estimation approaches may be implemented instead. Furthermore, other combinations (including multiple estimators based on a same approach) may also be implemented.

Unless specifically stated otherwise, as is apparent from the preceding discussion, it is to be appreciated that throughout this specification discussions utilizing terms such as "processing", "computing", "calculating", "correlating", "determining", "estimating", "selecting", "identifying", "obtaining", "representing", "receiving", "transmitting", "storing", "analyzing", "associating", "measuring", "detecting", "controlling", "delaying", "initiating", "setting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed, by one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:
   obtaining, from a blood-glucose sensor, one or more blood glucose sensor measurements;
   obtaining one or more reference sample signals based at least in part on one or more blood glucose reference samples;
   combining, via a processor, said one or more reference sample signals and said one or more blood glucose measurements to provide a plurality of blood glucose reference sample-sensor measurement pairs;
   estimating one or more parameters of a plurality of probability models based, at least in part, on said blood glucose reference sample-sensor measurement pairs;
   determining a plurality of functions for estimating a blood-glucose concentration in a patient from sensor measurements based, at least in part, on said estimated one or more parameters of said plurality of probability models;
   for each of said plurality of functions, estimating a sensor glucose concentration value by application of said function to provide a plurality of estimated sensor glucose concentration values, each of said estimated sensor glucose concentration values being generated by a corresponding one of said plurality of functions; and determining a composite sensor glucose concentration value for the patient based, at least partly, on a combination of said plurality of estimated sensor glucose concentration values.

2. The method of claim 1, wherein said obtaining comprises: taking sensor measurements for said plurality of blood glucose reference sample-sensor measurement pairs using at least one subcutaneous current sensor.

3. The method of claim 1, wherein one or more of said functions are defined at least partly by a slope and an offset.

4. The method of claim 1, wherein said one or more parameters for at least one of said functions comprise a calfactor variable and an offset variable.

5. The method of claim 4, wherein a relationship between current sensor measurements corresponding to said blood glucose reference sample-sensor measurement pairs and sensor glucose concentration for the patient may be represented by a linear model, said linear model associated with a slope and an offset; and wherein said slope and said offset of said linear model are determinable from said calfactor variable and/or said offset variable.

6. The method of claim 1, wherein said estimating one or more parameters of at least one of said probability models further comprises: estimating said one or more parameters of said at least one of said probability models using a linear Kalman filter estimator in which process noise and measurement noise are modeled as being constant.

7. The method of claim 1, wherein said estimating one or more parameters of at least one of said probability models further comprises: estimating said one or more parameters of said at least one of said probability models using a linear Kalman filter estimator in which process noise is adapted as a function of model performance.

8. The method of claim 1, wherein said estimating one or more parameters of at least one of said probability models further comprises: estimating said one or more parameters of said at least one of said probability models using a linear Kalman filter estimator in which measurement noise is adapted as a function of model performance.

9. The method of claim 1, wherein said estimating one or more parameters of at least one of said probability models further comprises: estimating said one or more parameters of said at least one of said probability models using a Bayesian estimator in which sensor measurements corresponding to said blood glucose reference sample-sensor measurement pairs comprise an independent variable and blood glucose reference samples corresponding to said blood glucose reference sample-sensor measurement pairs comprise a measured variable.

10. The method of claim 1, wherein said determining a composite sensor glucose concentration value for the patient comprises: weighting said plurality of sensor glucose concentration values based, at least in part, on a plurality of quality indicators indicative of an accuracy of said plurality of probability models.

11. The method of claim 10, wherein said plurality of quality indicators comprise a plurality of likelihood values; and wherein said method further comprises: calculating said plurality of likelihood values based, at least partly, on error differences between sensor glucose concentration values estimated from said plurality of probability models and reference blood glucose values from blood glucose reference samples.

12. The method of claim 1, wherein determining said composite sensor glucose concentration value comprises:
fractionally weighting said estimated sensor glucose concentration values based, at least in part, on likelihood values based on performance of said plurality of functions; and
combining said fractionally weighted estimated glucose concentration values to provide said composite sensor glucose concentration value.

13. The method of claim 1, wherein said plurality of probability models are to estimate said one or more signals to represent said one or more parameters relatively or effectively simultaneously.

14. An apparatus comprising:
a calibration unit to receive one or more signals based on blood-glucose sensor measurements, said calibration unit comprising one or more processors programmed to:
obtain a plurality of blood glucose reference sample-sensor measurement pairs;
estimate one or more parameters of a plurality of probability models based, at least in part, on said blood glucose reference sample-sensor measurement pairs;
determine a plurality of functions for estimating a blood-glucose concentration in a patient from sensor measurements based, at least in part, on said estimated one or more parameters of said plurality of probability models;
for each of said plurality of functions, estimate a sensor glucose concentration value by application of said function to provide a plurality of estimated sensor glucose concentration values, each of said estimated sensor glucose concentration values being generated by a corresponding one of said plurality of functions; and
determine a composite sensor glucose concentration value for the patient based, at least in part, on a combination of said plurality of estimated sensor glucose concentration values.

15. The apparatus of claim 14, wherein said one or more processors are further programmed to obtain said plurality of blood glucose reference sample-sensor measurement pairs by taking sensor measurements for said plurality of blood glucose reference sample-sensor measurement pairs using at least one subcutaneous current sensor.

16. The apparatus of claim 14, wherein at least one of said functions is defined at least partly by a slope and an offset.

17. The apparatus of claim 14, wherein at least one of said functions is defined, at least in part, by a calfactor variable and an offset variable.

18. The apparatus of claim 17, wherein a relationship between current sensor measurements corresponding to said blood glucose reference sample-sensor measurement pairs and sensor glucose concentration for the patient may be represented by a linear model, said linear model associated with a slope and an offset; and wherein said slope and said offset of said linear model are determinable from said calfactor variable and/or said offset variable.

19. The apparatus of claim 14, wherein said one or more processors are further programmed to estimate said one or more parameters of at least one of said probability models by: estimating said one or more parameters using a linear Kalman filter estimator in which process noise and measurement noise are modeled as being constant.

20. The apparatus of claim 14, wherein said one or more processors are further programmed to estimate said one or more parameters of at least one of said probability models by: estimating said one or more parameters using a linear Kalman filter estimator in which process noise is adapted as a function of model performance.

21. The apparatus of claim 14, wherein said one or more processors are further programmed to estimate said one or more parameters of at least one of said probability models by: estimating said one or more parameters using a linear Kalman filter estimator in which measurement noise is adapted as a function of model performance.

22. The apparatus of claim 14, wherein said one or more processors are further programmed to estimate said one or more parameters of at least one of said probability models by: estimating said one or more parameters using a Bayesian estimator in which sensor measurements corresponding to said blood glucose reference sample-sensor measurement pairs comprise an independent variable and blood glucose reference samples corresponding to said blood glucose reference sample-sensor measurement pairs comprise a measured variable.

23. The apparatus of claim 14, wherein said one or more processors are programmed to determine said composite sensor glucose concentration value for the patient by: weighting said plurality of sensor glucose concentration values based, at least in part, on a plurality of quality indicators indicative of an accuracy of said plurality of probability models.

24. The apparatus of claim 23, wherein said plurality of quality indicators comprise a plurality of likelihood values; and wherein said one or more processors are further programmed to: calculate said plurality of likelihood values based, at least partly, on error differences between sensor glucose concentration values estimated from said plurality of probability models and reference blood glucose values from blood glucose reference samples.

25. The apparatus of claim 14, further comprising: one or more blood-glucose sensors adapted to be coupled to the patient to obtain blood-glucose sensor measurements and adapted to provide said one or more signals based on said blood-glucose sensor measurements, wherein said one or more processors are further programmed to obtain said plurality of blood glucose reference sample-sensor measurement pairs via said one or more blood-glucose sensors using said one or more signals.

26. A system comprising:
   means for obtaining a plurality of blood glucose reference sample-sensor measurement pairs;
   means for estimating one or more parameters of a plurality of probability models based, at least in part, on said blood glucose reference sample-sensor measurement pairs;
   means for determining a plurality of functions for estimating a blood-glucose concentration in a patient from sensor measurements based, at least in part, on said estimated one or more parameters of said plurality of probability models;
   for each of said plurality of functions, means for estimating a sensor glucose concentration value by application of said function to provide a plurality of estimated sensor glucose concentration values, each of said estimated sensor glucose concentration values being generated by a corresponding one of said plurality of functions; and
   means for determining a composite sensor glucose concentration value for the patient based, at least partly, on a combination of said plurality of estimated sensor glucose concentration values.

27. An article comprising:
   at least one non-transitory storage medium having stored thereon instructions executable by one or more processors to:
   obtain a plurality of blood glucose reference sample-sensor measurement pairs;
   estimate one or more parameters of a plurality of probability models based, at least in part, on said blood glucose reference sample-sensor measurement pairs;
   determine a plurality of functions for estimating a blood-glucose concentration in a patient from sensor measurements based, at least in part, on said estimated one or more parameters of said plurality of probability models;
   for each of said plurality functions estimate a sensor glucose concentration value by application of said function to provide a plurality of estimated sensor glucose concentration values, each of said estimated sensor glucose concentration values being generated by a corresponding one of said plurality of functions; and
   determine a composite sensor glucose concentration value for the patient based, at least part, on a combination of said plurality of estimated sensor glucose concentration values.

* * * * *